(12) United States Patent
Park et al.

(10) Patent No.: US 10,069,077 B2
(45) Date of Patent: Sep. 4, 2018

(54) COMPOUND FOR ORGANIC LIGHT-EMITTING DEVICE AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Illsoo Park, Yongin (KR); Seulong Kim, Yongin (KR); Hyosup Shin, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 502 days.

(21) Appl. No.: 14/644,158

(22) Filed: Mar. 10, 2015

(65) Prior Publication Data

US 2016/0079543 A1    Mar. 17, 2016

(30) Foreign Application Priority Data

Sep. 12, 2014    (KR) .......................... 10-2014-0121266

(51) Int. Cl.
| | | |
|---|---|---|
| H01L 51/00 | (2006.01) | |
| C07D 213/53 | (2006.01) | |
| C09K 11/06 | (2006.01) | |
| H01L 51/50 | (2006.01) | |
| H05B 33/20 | (2006.01) | |

(52) U.S. Cl.
CPC ........ H01L 51/0067 (2013.01); C07D 213/53 (2013.01); C09K 11/06 (2013.01); H01L 51/0052 (2013.01); H01L 51/5012 (2013.01); H05B 33/20 (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *H01L 2251/308* (2013.01); *H01L 2251/552* (2013.01)

(58) Field of Classification Search
CPC ............. H01L 51/0052; H01L 51/5012; H01L 51/0072; C07D 209/86
See application file for complete search history.

(56) References Cited

U.S. PATENT DOCUMENTS

| | | | |
|---|---|---|---|
| 6,813,330 B1 | 11/2004 | Barker et al. | |
| 2007/0222373 A1 | 9/2007 | Arakane et al. | |
| 2009/0322211 A1* | 12/2009 | Takahashi | C09K 11/06 313/504 |
| 2012/0217449 A1 | 8/2012 | Spreitzer et al. | |
| 2013/0240850 A1 | 9/2013 | Forrest et al. | |
| 2014/0054559 A1 | 2/2014 | Kim et al. | |
| 2014/0061594 A1 | 3/2014 | Forrest et al. | |

FOREIGN PATENT DOCUMENTS

| | | |
|---|---|---|
| KR | 10-2006-0109524 A | 10/2006 |
| KR | 10-2006-0118913 A | 11/2006 |
| KR | 10-2008-0100789 A | 11/2008 |
| KR | 10-2008-0103975 A | 11/2008 |
| KR | 10-2011-0032373 A | 3/2011 |
| KR | 10-2011-0098240 A | 9/2011 |
| KR | 10-2012-0115249 A | 10/2012 |
| KR | 10-2014-0026681 A | 3/2014 |
| WO | WO 2014/124599 | * 8/2014 |

OTHER PUBLICATIONS

Fei et al (Single Crystals of the Disubstituted Anthracene 9,10-(Ph2P=S)2C14H8 Selectively and Reversibly Detect Toluene by Solid-State Fluorescence Emission, Angew. Chem. Int. Ed. 2003, 42, No. 7), Jul. 2003.*
USPTO search report, dated Mar. 2017.*
Lee et al (Highly efficient blue organic light emitting diodes using dual emissive layers with host-dopant system, Journal of Photonics for Energy, vol. 3, 2013, pp. 033598-1-033598-8, published on Apr. 9, 2013.*
Chiang, Chien-Jung et al., "Ultrahigh Efficiency Fluorescent Single and Bi-Layer Organic Light Emitting Diodes: The Key Role of Triplet Fusion", Advanced Functional Materials, 2013, pp. 739-746, vol. 23.
Kondakov, D.Y. et al, "Triplet annihilation exceeding spin statistical limit in highly efficient fluorescent organic light-emitting diodes", Journal of Applied Physics, Dec. 29, 2009, pp. 124510-1 through 124510-7, vol. 106.
Monkman, A.P., "Singlet Generation from Triplet Excitons in Fluorescent Organic Light-Emitting Diodes", ISRN Materials Science, 2013, pp. 1-19, vol. 2013, Article ID 670130.

* cited by examiner

*Primary Examiner* — Gregory Listvoyb
(74) *Attorney, Agent, or Firm* — Lewis Roca Rothgerber Christie LLP

(57) ABSTRACT

A compound for an organic light-emitting device, the compound represented by Chemical Formula 1 and satisfying Mathematical Formula 1:

$$A \!-\!\!\!\!\text{\small(}\!B\text{\small)}_{n},\qquad\text{Chemical Formula 1}$$

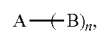

$$E_{S1} < 2E_{T1} < E_{T2}, \qquad\text{Mathematical Formula 1}$$

wherein, in Mathematical Formula 1, $E_{S1}$ is a first singlet energy of the compound; $E_{T1}$ is a first triplet energy of the compound; and $E_{T2}$ is a second triplet energy of the compound.

8 Claims, 2 Drawing Sheets

COMPOUND FOR ORGANIC LIGHT-EMITTING DEVICE AND ORGANIC LIGHT-EMITTING DEVICE INCLUDING THE SAME

CROSS-REFERENCE TO RELATED APPLICATION

This application claims priority to and the benefit of Korean Patent Application No. 10-2014-0121266, filed on Sep. 12, 2014, in the Korean Intellectual Property Office, the entire disclosure of which is incorporated herein by reference.

BACKGROUND

1. Field

One or more aspects of embodiments of the present disclosure relate to compounds for organic light-emitting devices and organic light-emitting devices including the same.

2. Description of the Related Art

Organic light-emitting devices, which are self-emitting devices, have advantages such as a wide viewing angles, high contrast, quick response times, high brightness, and/or low driving voltage, and can provide multicolored images.

An organic light-emitting device may typically have a structure in which a first electrode is positioned on a substrate, and a hole transport region, an emission layer (EML), an electron transport region, and a second electrode are sequentially positioned on the first electrode. Holes injected from the first electrode move to the EML via the hole transport region, and electrons injected from the second electrode move to the EML via the electron transport region. Carriers (e.g., the holes and electrons) recombine in a light-emission region and generate excitons. When excitons drop from an excited state to a ground state, light is emitted.

SUMMARY

One or more aspects of embodiments of the present disclosure are directed to compounds for organic light-emitting devices and organic light-emitting devices including the same.

Additional aspects will be set forth in part in the description which follows and, in part, will be apparent from the description, or may be learned by practice of the presented embodiments.

According to one or more exemplary embodiments, a compound for an organic light-emitting device satisfies Mathematical Formula 1:

$$E_{S1} < 2E_{T1} < E_{T2}. \qquad \text{Mathematical Formula 1}$$

In Mathematical Formula 1, $E_{S1}$ is a first singlet energy of the compound;

$E_{T1}$ is a first triplet energy of the compound; and $E_{T2}$ is a second triplet energy of the compound.

According to one or more exemplary embodiments, an organic light-emitting device includes a first electrode; a second electrode; and an organic layer between the first electrode and the second electrode, the organic layer including an emission layer, and the emission layer including the compound for an organic light-emitting device.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
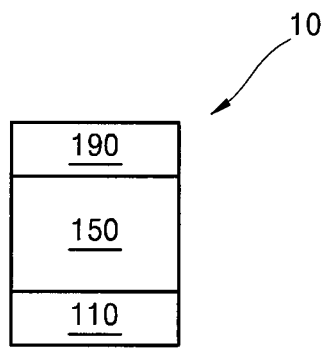
FIG. 1 is a schematic cross-sectional view of an organic light-emitting device according to some embodiments.

Reference will now be made in detail to embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the present invention refers to "one or more embodiments of the present invention."

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when a layer, region, or component is referred to as being "formed on" another layer, region, or component, it can be directly or indirectly formed on the other layer, region, or component. In other words, intervening layers, regions, or components may be present.

Sizes of elements in the drawings may be exaggerated for convenience of explanation. In other words, since sizes and thicknesses of components in the drawings are arbitrarily illustrated for convenience of explanation, the following embodiments are not limited thereto.

The term "organic layer" used herein refers to a single layer and/or multiple layers positioned between the first and second electrodes of the organic light-emitting device. Materials contained in the "organic layer" are not limited to organic materials. In addition, as used herein, the terms "use," "using," and "used" may be considered synonymous with the terms "utilize," "utilizing," and "utilized," respectively. Also, the term "exemplary" is intended to refer to an example or illustration.

A compound for an organic light-emitting device according to some embodiments of the present disclosure satisfies Mathematical Formula 1.

$$E_{S1} < 2E_{T1} < E_{T2}. \qquad \text{Mathematical Formula 1}$$

In Mathematical Formula 1, $E_{S1}$ is a first singlet energy of the compound;

$E_{T1}$ is a first triplet energy of the compound; and $E_{T2}$ is a second triplet energy of the compound.

Figure 2:
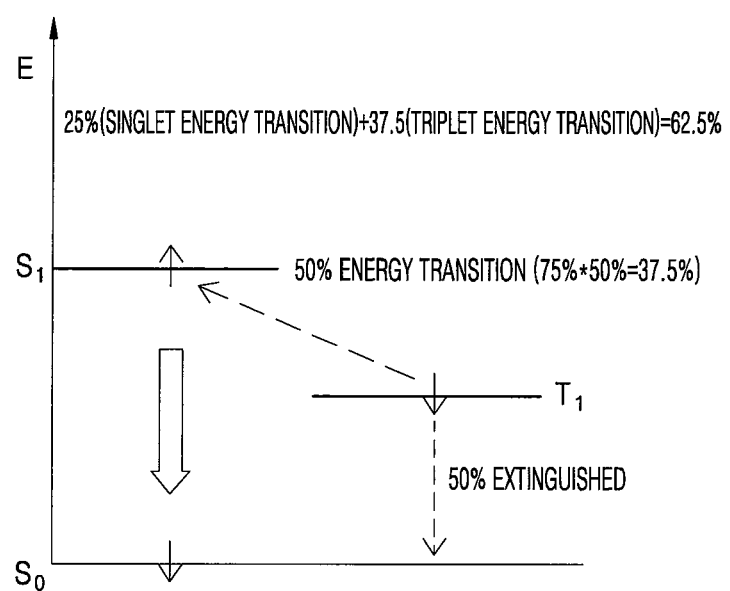
FIG. 2 is a schematic diagram of a light-emitting model of an organic light-emitting device according to some embodiments.

When the compound for an organic light-emitting device satisfies Mathematical Formula 1, electrons can transition from a triplet state into a singlet state, and energy transition does not occur into a second triplet state, thus preventing or reducing energy loss. Accordingly, when the compound for an organic light-emitting device satisfies Mathematical Formula 1, all of the excited triplets may be changed into singlets (as illustrated in FIG. 2), and internal quantum efficiency of an organic light-emitting device including the compound may be increased up to 62.5%.

For example, the compound for an organic light-emitting device may satisfy Mathematical Formula 1-1, without being limited thereto:

$$E_{T1} < E_{S1} < 2E_{T1} < E_{T2} < E_{Q1}.$$ Mathematical Formula 1-1

In Mathematical Formula 1-1,
$E_{S1}$ is a first singlet energy of the compound;
$E_{T1}$ is a first triplet energy of the compound;
$E_{T2}$ is a second triplet energy of the compound; and
$E_{Q1}$ is a first quintet energy of the compound.

For example, in Mathematical Formula 1, $E_{S1}$ may be in a range of about 2.7 eV to about 3.3 eV, without being limited thereto. When $E_{S1}$ is within the range described above, the organic light-emitting device including the compound for an organic light-emitting device may emit blue light, particularly, blue fluorescent light.

For example, in Mathematical Formula 1, $E_{T1}$ may be in a range of about 1.3 eV to about 1.7 eV, without being limited thereto.

For example, in Mathematical Formula 1, $E_{T2}$ may be in a range of about 2.8 eV to about 3.5 eV, without being limited thereto.

For example, the compound for an organic light-emitting device may be represented by Chemical Formula 1, without being limited thereto:

Chemical Formula 1

In Chemical Formula 1, A is a substituted or unsubstituted $C_6$-$C_{15}$ arene having a valence of n or a substituted or unsubstituted $C_1$-$C_{15}$ heteroarene having a valence of n;

B is a substituted or unsubstituted $C_6$-$C_{15}$ aryl group or a substituted or unsubstituted $C_1$-$C_{15}$ heteroaryl group; and n is an integer selected from 1, 2, and 3, at least one substituent of the substituted $C_6$-$C_{15}$ arene, the substituted $C_1$-$C_{15}$ heteroarene, the substituted $C_6$-$C_{15}$ aryl group and the substituted $C_1$-$C_{15}$ heteroaryl group is selected from:

—F; —Cl; —Br; —I; a $C_1$-$C_{10}$ alkyl group; a $C_6$-$C_{15}$ aryl group; and —Si($Q_{11}$)($Q_{12}$)($Q_{13}$);

a $C_1$-$C_{10}$ alkyl group and a $C_6$-$C_{15}$ aryl group, each substituted with at least one selected from a $C_1$-$C_{10}$ alkyl group and a $C_6$-$C_{15}$ aryl group; and a $C_1$-$C_{10}$ alkyl group and a $C_6$-$C_{15}$ aryl group, each substituted with a $C_6$-$C_{15}$ aryl group that is substituted with at least one selected from a $C_1$-$C_{10}$ alkyl group and a $C_6$-$C_{15}$ aryl group, where $Q_{11}$ to $Q_{13}$ are each independently selected from a hydrogen atom, a $C_1$-$C_{10}$ alkyl group, and a $C_6$-$C_{15}$ aryl group.

For example, in Chemical Formula 1, a first singlet energy of A ($E_{AS1}$) and a first singlet energy of B ($E_{BS1}$) may each independently be in a range of about 2.7 eV to about 3.3 eV, without being limited thereto.

For example, in Chemical Formula 1, a first triplet energy of A ($E_{AT1}$) and a first triplet energy of B ($E_{BT1}$) may satisfy Mathematical Formula 2, without being limited thereto:

$$E_{AT1} < E_{BT1}.$$ Mathematical Formula 2

In some embodiments, $E_{T1}$ and $E_{T2}$ of the compound of Chemical Formula 1 may be determined by $E_{AT1}$ and $E_{BT1}$.

According to some embodiments, in Chemical Formula 1, the first triplet energy of B ($E_{BT1}$) and a second triplet energy of A ($E_{AT2}$) may further satisfy Mathematical Formula 3, without being limited thereto:

$$E_{AT2} < E_{BT1}.$$ Mathematical Formula 3

In some embodiments, $E_{T1}$ and $E_{T2}$ of the compound of Chemical Formula 1 may be determined by $E_{AT1}$, $E_{AT2}$, and $E_{BT1}$.

For example, in Chemical Formula 1, A may be anthracene, without being limited thereto.

For example, in Chemical Formula 1, B may be selected from a phenyl group; a pyridinyl group; and a phenyl group and a pyridinyl group, each substituted with at least one selected from —F, a methyl group, a tert-butyl group, a phenyl group, a phenyl group substituted with a methyl group, and —Si($CH_3$)$_3$, without being limited thereto.

For example, in Chemical Formula 1, n may be 2, without being limited thereto.

$E_{S1}$, $E_{T1}$ and $E_{T2}$ of anthracene, phenyl, pyridine, and biphenyl were calculated using B3LYP/6-31G base set by using Gaussian 09, and the results are shown in Table 1.

TABLE 1

|  | $E_{S1}$(eV) | $E_{T1}$(eV) | $E_{T2}$(eV) |
| --- | --- | --- | --- |
| anthracene | 3.22 | 1.74 | 3.26 |
| phenyl | 5.21 | 3.79 | 4.78 |
| pyridine | 5.09 | 3.91 | 4.14 |
| biphenyl | 4.51 | 3.32 | 3.91 |

Since anthracene has a low first triplet energy level, a wide range of substituents may be selected. In addition, a dopant including anthracene as a core may be efficiently used for blue light emission.

Since phenyl, pyridine, and biphenyl are all chemically and physically stable and inexpensive, compounds having phenyl, pyridine, and/or biphenyl as substituents may have high chemical and physical stability and a very competitive price.

For example, the compound for an organic light-emitting device may be represented by one selected from Chemical Formulae 1A and 2A, without being limited thereto:

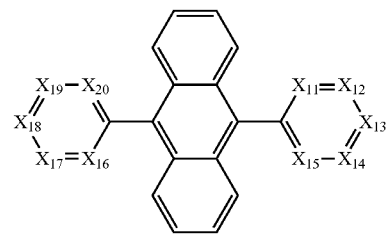

Chemical Formula 1A

Chemical Formula 2A

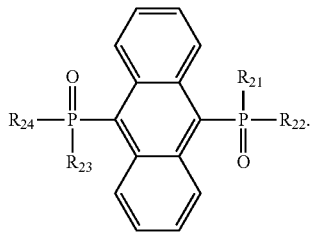

In Chemical Formulae 1A and 2A, $X_{11}$ is a nitrogen atom (N) or $CR_{11}$; $X_{12}$ is N or $CR_{12}$; $X_{13}$ is N or $CR_{13}$; $X_{14}$ is N or $CR_{14}$; $X_{15}$ is N or $CR_{15}$; $X_{16}$ is N or $CR_{16}$; $X_{17}$ is N or $CR_{17}$; $X_{18}$ is N or $CR_{18}$; $X_{19}$ is N or $CR_{19}$; and $X_{20}$ is N or $CR_{20}$;

$R_{11}$ to $R_{20}$ are each independently selected from a hydrogen atom, —F, —Cl, —Br, —I, a substituted or unsubstituted $C_1$-$C_{10}$ alkyl group, a substituted or unsubstituted $C_6$-$C_{15}$ aryl group, and —Si$(Q_{11})(Q_{12})(Q_{13})$;

$R_{21}$ to $R_{24}$ are each independently selected from a hydrogen atom, a substituted or unsubstituted $C_1$-$C_{10}$ alkyl group, and a substituted or unsubstituted $C_6$-$C_{15}$ aryl group;

where $Q_{11}$ to $Q_{13}$ are each independently selected from a hydrogen atom, a $C_1$-$C_{10}$ alkyl group, and a $C_6$-$C_{15}$ aryl group; and at least one substituent of the substituted $C_1$-$C_{10}$ alkyl group and the substituted $C_6$-$C_{15}$ aryl group is selected from:

a $C_1$-$C_{10}$ alkyl group; a $C_6$-$C_{15}$ aryl group; and a $C_6$-$C_{15}$ aryl group substituted with at least one selected from a $C_1$-$C_{10}$ alkyl group and a $C_6$-$C_{15}$ aryl group.

In some embodiments, in Chemical Formula 1A, $X_{11}$ is $CR_{11}$; $X_{12}$ is $CR_{12}$; $X_{13}$ is $CR_{13}$; $X_{14}$ is $CR_{14}$; $X_{15}$ is $CR_{15}$; $X_{16}$ is $CR_{16}$; $X_{17}$ is $CR_{17}$; $X_{18}$ is $CR_{18}$; $X_{19}$ is $CR_{19}$; and $X_{20}$ is $CR_{20}$, without being limited thereto.

In some embodiments, in Chemical Formula 1A, $X_{11}$ is N; $X_{12}$ is $CR_{12}$; $X_{13}$ is $CR_{13}$; $X_{14}$ is $CR_{14}$; $X_{15}$ is $CR_{15}$; $X_{16}$ is N; $X_{17}$ is $CR_{17}$; $X_{18}$ is $CR_{18}$; $X_{19}$ is $CR_{19}$; and $X_{20}$ is $CR_{20}$, without being limited thereto.

In some embodiments, in Chemical Formula 1A, $X_{11}$ is $CR_{11}$; $X_{12}$ is N; $X_{13}$ is $CR_{13}$; $X_{14}$ is $CR_{14}$; $X_{15}$ is $CR_{15}$; $X_{16}$ is $CR_{16}$; $X_{17}$ is N; $X_{18}$ is $CR_{18}$; $X_{19}$ is $CR_{19}$; and $X_{20}$ is $CR_{20}$, without being limited thereto.

For example, in Chemical Formula 1A, $R_{11}$ to $R_{20}$ may be each independently selected from a hydrogen atom, —F, a methyl group, an ethyl group, an n-propyl group, an iso-propyl group, an n-butyl group, an iso-butyl group, a sec-butyl group, a tert-butyl group, —Si$(CH_3)_3$, and groups represented by Chemical Formulae 3-1 and 3-2 below, without being limited thereto:

3-1

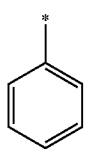

3-2

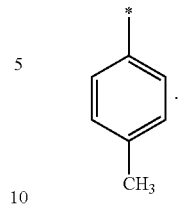

In Chemical Formulae 3-1 and 3-2, * is a binding site to an adjacent atom.

For example, in Chemical Formula 1A, $R_{21}$ to $R_{24}$ may be each independently selected from a methyl group, an ethyl group, an n-propyl group, an iso-propyl group, an n-butyl group, an iso-butyl group, a sec-butyl group, a tert-butyl group, and groups represented by Chemical Formulae 3-1 and 3-2, without being limited thereto:

3-1

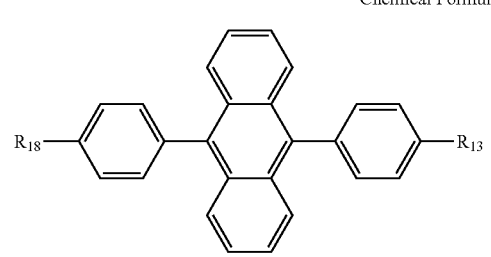

3-2

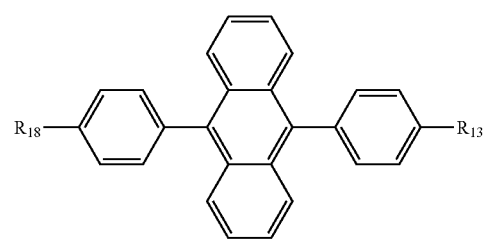

For example, the compound for an organic light-emitting device may be represented by any one selected from Chemical Formulae 1A-1 to 1A-6 and 2A:

Chemical Formula 1A-1

Chemical Formula 1A-2

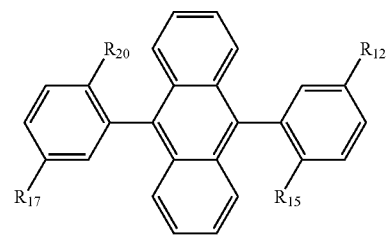

Chemical Formula 1A-3

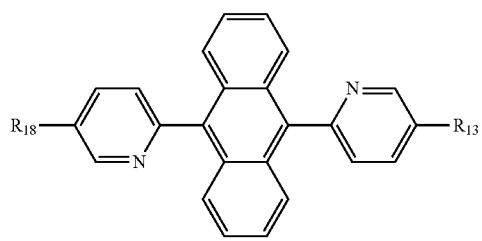

Chemical Formula 1A-4

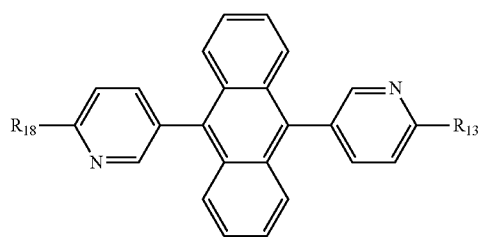

Chemical Formula 1A-5

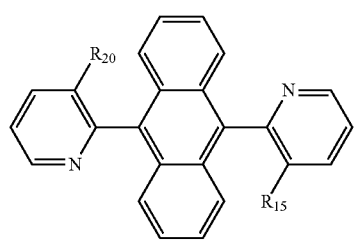

Chemical Formula 1A-6

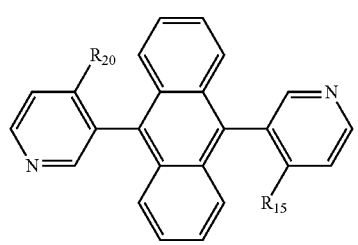

Chemical Formula 2A

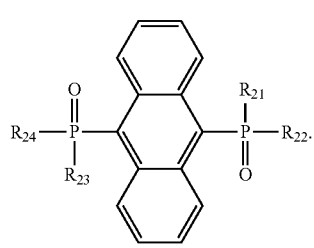

In Chemical Formulae 1A-1 to 1A-6 and 2A, $R_{12}$, $R_{13}$, $R_{15}$, $R_{17}$, $R_{18}$ and $R_{20}$ are as defined in Chemical Formula 1A; and $R_{21}$ to $R_{24}$ are as defined in Chemical Formula 2A.

For example, in Chemical Formulae 1A-1 to 1A-6 and 2A, $R_{12}$, $R_{13}$, $R_{15}$, $R_{17}$, $R_{18}$ and $R_{20}$ may be each independently selected from a hydrogen atom, —F, a methyl group, an ethyl group, an n-propyl group, an iso-propyl group, an n-butyl group, an iso-butyl group, a sec-butyl group, a tert-butyl group, —Si(CH$_3$)$_3$, and groups represented by Chemical Formulae 3-1 and 3-2:

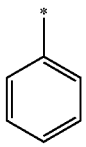

3-1

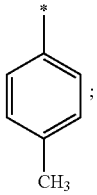

3-2

$R_{21}$ to $R_{24}$ may be each independently selected from a methyl group, an ethyl group, an n-propyl group, an iso-propyl group, an n-butyl group, an iso-butyl group, a sec-butyl group, a tert-butyl group, and groups represented by Chemical Formulae 3-1 and 3-2, without being limited thereto.

For example, the compound for an organic light-emitting device may be selected from Compounds 1 to 11 below, without being limited thereto.

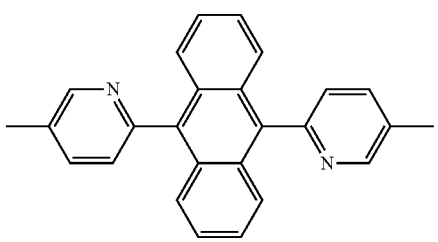

1

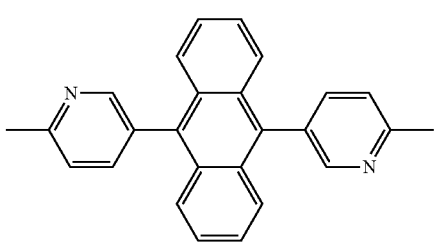

2

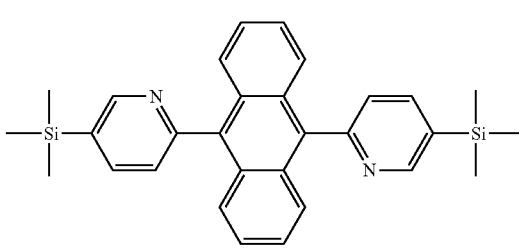

3

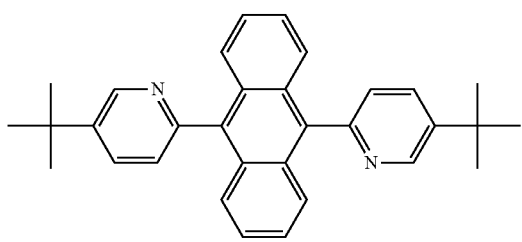
4

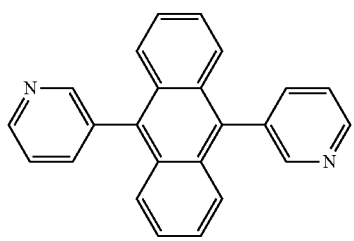
5

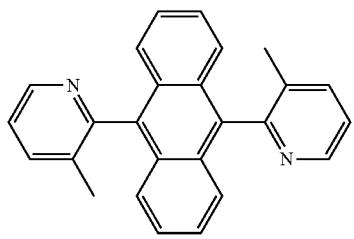
6

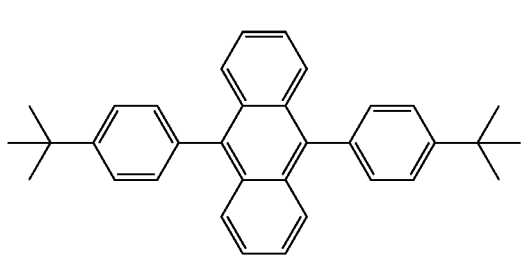
7

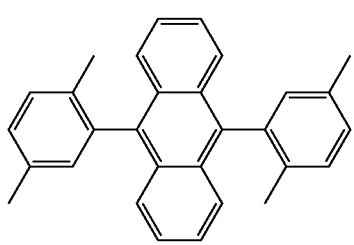
8

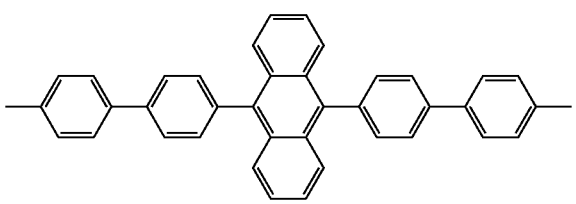
9

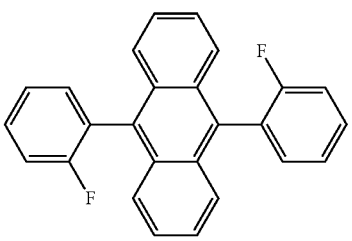
10

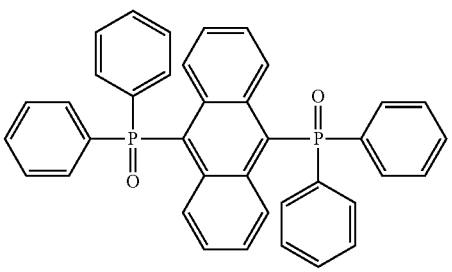
11

$E_{S1}$, $E_{T1}$, and $E_{T2}$ of each of Compounds 1 to 11 and ADN were calculated using B3LYP/6-31G base set by using Gaussian 09, and the results are shown in Table 2.

TABLE 2

| Compound | $E_{S1}$(eV) | $E_{T1}$(eV) | $E_{T2}$(eV) |
|---|---|---|---|
| 1 | 3.10 | 1.68 | 3.43 |
| 2 | 3.10 | 1.68 | 3.43 |
| 3 | 3.10 | 1.68 | 3.44 |
| 4 | 3.10 | 1.68 | 3.43 |
| 5 | 3.10 | 1.67 | 3.43 |
| 6 | 3.12 | 1.67 | 3.43 |
| 7 | 3.11 | 1.69 | 3.45 |
| 8 | 3.11 | 1.68 | 3.45 |
| 9 | 3.11 | 1.68 | 3.45 |
| 10 | 3.12 | 1.67 | 3.44 |
| 11 | 2.75 | 1.46 | 2.99 |
| ADN | 3.38 | 1.68 | 2.67 |

The compound for an the organic light-emitting device satisfying Mathematical Formula 1 above may be synthesized using any suitable organic synthesis method known to those of ordinary skill in the art.

For example, the compound for an organic light-emitting device may be positioned between a pair of electrodes of the organic light-emitting device. In some embodiments, the compound for an organic light-emitting device may be included in an emission layer (EML). Thus, in some embodiments, an organic light-emitting device may include a first electrode, a second electrode opposite to and facing the first electrode, and an organic layer between the first electrode and the second electrode, the organic layer including at least one compound selected from compounds for an organic light-emitting device as described above.

Used herein, the expression "X includes at least one compound selected from compounds for an organic light-emitting device" may be interpreted as "X includes one type (kind) of compound for an organic light-emitting device represented by Chemical Formula 1, or at least two different types (kinds) of compounds for an organic light-emitting device represented by Chemical Formula 1".

In some embodiments, the organic layer includes a hole transport region between the first electrode (e.g., an anode) and the EML, the hole transport region including at least one layer selected from a hole injection layer (HIL), a hole transport layer (HTL), a buffer layer, and an electron blocking layer (EBL); and an electron transport region between the EML and the second electrode (e.g., a cathode), the electron transport region including at least one layer selected from a hole blocking layer (HBL), an electron transport layer (ETL), and an electron injection layer (EIL).

FIG. 1 is a schematic cross-sectional view of an organic light-emitting device 10 according to some embodiments of the present disclosure. The organic light-emitting device 10 includes a first electrode 110, an organic layer 150, and a second electrode 190.

Hereinafter, a structure of the organic light-emitting device and a method of manufacturing the same according to some embodiments of the present disclosure will be described with reference to FIG. 1.

In FIG. 1, a substrate may be positioned on a lower surface of the first electrode 110 (i.e. under the first electrode 110) or on an upper surface of the second electrode 190 (i.e. on the second electrode 190). The substrate may be a glass substrate or a transparent plastic substrate having good mechanical strength, thermal stability, transparency, surface smoothness, ease of handling, and water resistance.

For example, the first electrode 110 may be formed on the substrate by depositing or sputtering a material used to form the first electrode 110. When the first electrode 110 is an anode, the material used to form the first electrode 110 may be a high work function material capable of facilitating hole injection. The first electrode 110 may be a reflective, semi-transmissive, or transmissive electrode. Transparent and conductive materials such as indium tin oxide (ITO), indium zinc oxide (IZO), tin oxide ($SnO_2$), and/or zinc oxide (ZnO) may be used to form the first electrode 110. Alternatively, in order to form a semi-transmissive or reflective first electrode 110, at least one material selected from magnesium (Mg), aluminum (Al), aluminum (Al)-lithium (Li), calcium (Ca), magnesium (Mg)-indium (In), and magnesium (Mg)-silver (Ag) may be used.

The first electrode 110 may have a single-layered or a multi-layered structure. For example, the first electrode 110 may have a triple-layered structure of ITO/Ag/ITO, without being limited thereto.

The organic layer 150 may be positioned on the first electrode 110. The organic layer 150 includes an EML.

The organic layer 150 may further include a hole transport region between the first electrode and the EML, and an electron transport region between the EML and the second electrode.

The hole transport region may include at least one layer selected from an HIL, an HTL, a buffer layer, and an EBL, and the electron transport region may include at least one layer selected from an HBL, an ETL, and an EIL, without being limited thereto.

The hole transport region may have a single-layered structure formed of a single material, a single-layered structure formed of a plurality of different materials, or a multi-layered structure formed of a plurality of different materials.

For example, the hole transport region may have a single-layered structure formed of a plurality of different materials, or a structure of HIL/HTL, HIL/HTL/buffer layer, HIL/buffer layer, HTL/buffer layer, or HIL/HTL/EBL, where the layers in each structure are sequentially stacked on the first electrode 110, but the hole transport region is not limited thereto.

When the hole transport region includes an HIL, the HIL may be formed on the first electrode 110 by using one or more suitable methods such as vacuum deposition, spin coating, casting, Langmuir-Blodgett (LB) technique, inkjet printing, laser printing, and/or laser induced thermal imaging (LITI).

When the HIL is formed by vacuum deposition, deposition conditions may be selected according to a compound used to form the HIL and a structure of the HIL to be formed, and in some embodiments may be as follows: a deposition temperature of about 100 to about 500° C., a vacuum pressure of about $10^{-8}$ to about $10^{-3}$ torr, and a deposition rate of about 0.01 to about 100 Å/sec.

When the HIL is formed by spin coating, coating conditions may be selected according to a compound used to form the HIL and a structure of the HIL to be formed, and in some embodiments may be as follows: a coating rate of about 2000 rpm to about 5000 rpm and a heat-treatment temperature of about 80° C. to about 200° C.

When the hole transport region includes an HTL, the HTL may be formed on the first electrode 110 or on the HIL by using one or more suitable methods such as vacuum deposition, spin coating, casting, LB technique, inkjet printing, laser printing, and/or LITI. When the HTL is formed by vacuum deposition and/or spin coating, the deposition conditions and coating conditions may be similar to those for the formation of the HIL.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4''-tris(N-carbazolyl)triphenylamine) (TCTA), polyaniline/dodecylbenzenesulfonic acid (Pani/DBSA), poly 3,4-ethylenedioxythiophene)/poly 4-styrene-sulfonate (PEDOT/PSS), polyaniline/camphor sulfonic acid (Pani/CSA), polyaniline/poly 4-styrenesulfonate (PANI/PSS), a compound represented by Chemical Formula 201, and a compound represented by Chemical Formula 202.

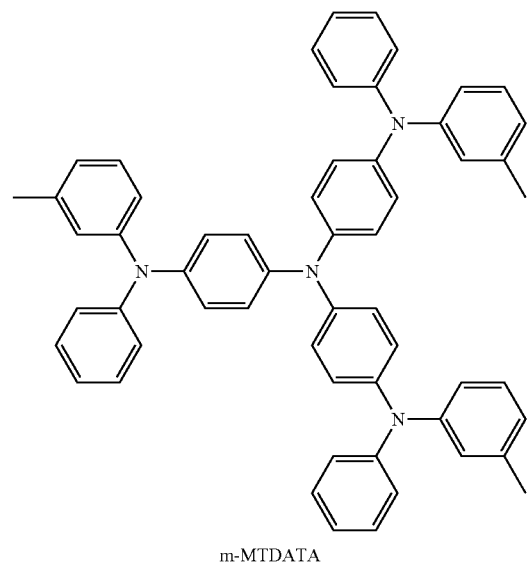

m-MTDATA

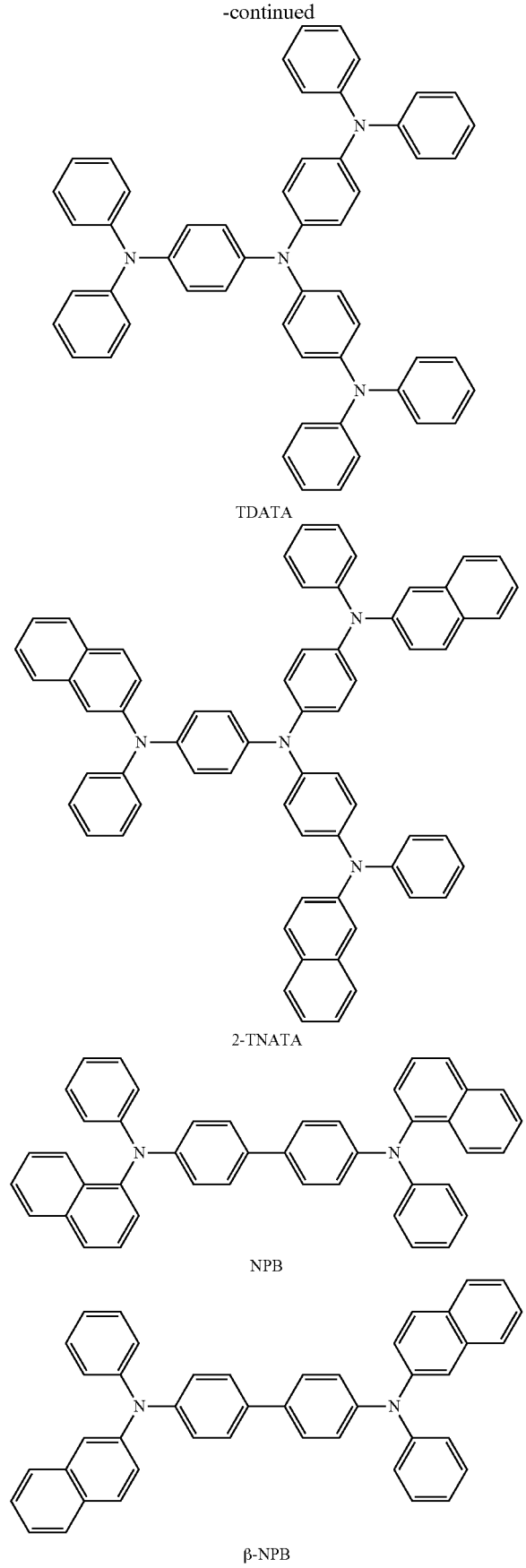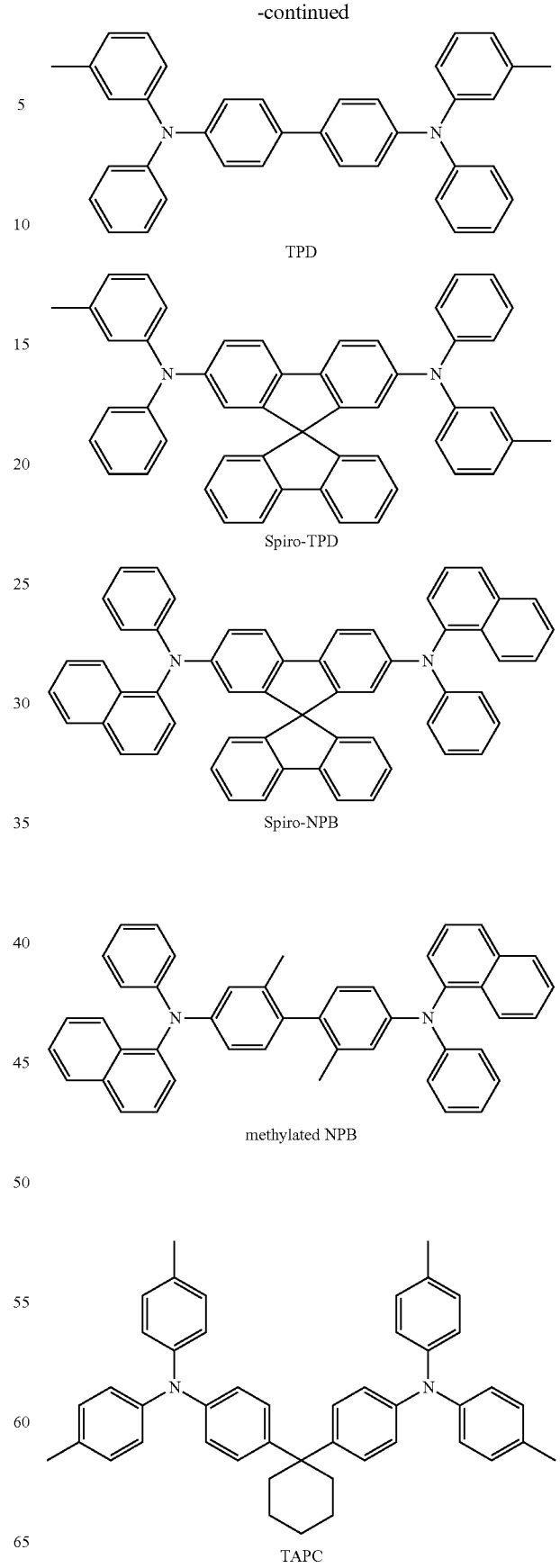

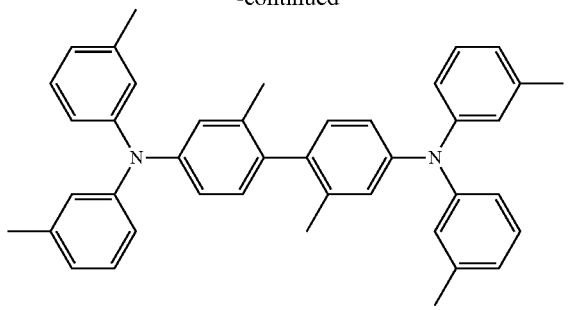

HMTPD

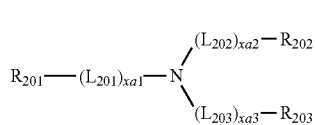

Chemical Formula 201

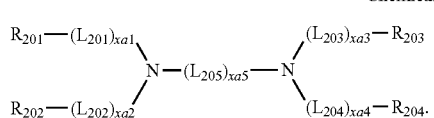

Chemical Formula 202

In Chemical Formulae 201 and 202, $L_{201}$ to $L_{205}$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group;

xa1 to xa4 are each independently selected from 0, 1, 2, and 3;

xa5 is selected from 1, 2, 3, 4, and 5;

$R_{201}$ to $R_{204}$ are each independently a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, or a substituted or unsubstituted monovalent non-aromatic hetero-condensed polycyclic group.

For example, in Chemical Formulae 201 and 202, $L_{201}$ to $L_{205}$ may be each independently selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3;

$R_{201}$ to $R_{204}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present disclosure are not limited thereto.

The compound of Chemical Formula 201 may be represented by Chemical Formula 201A.

Chemical Formula 201A

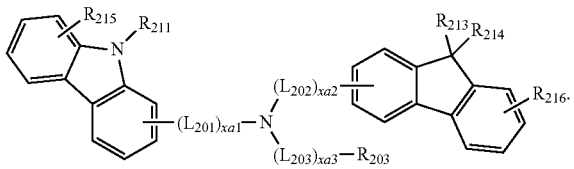

In some embodiments, the compound of Chemical Formula 201 may be represented by Chemical Formula 201A-1, without being limited thereto.

Chemical Formula 201A-1

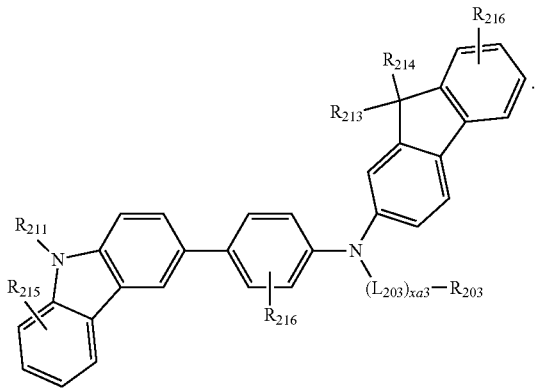

The compound of Chemical Formula 202 may be represented by Chemical Formula 202A, without being limited thereto:

Chemical Formula 202A

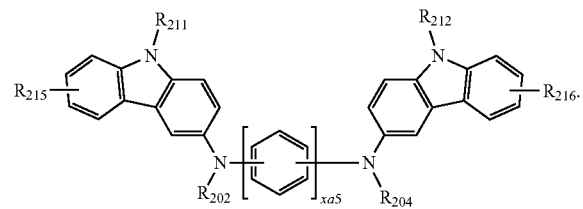

In Chemical Formulae 201A, 201A-1, and 202A, $L_{201}$ to $L_{203}$, xa1 to xa3, xa5, and $R_{202}$ to $R_{204}$ are as described above, $R_{211}$ is as described above with reference to $R_{203}$, and $R_{213}$ to $R_{216}$ are each independently a hydrogen atom, a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic hetero-condensed polycyclic group.

In some embodiments, in Chemical Formulae 201A, 201A-1, and 202A, $L_{201}$ to $L_{203}$ are each independently selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrycenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrycenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 are each independently 0 or 1;

$R_{203}$, $R_{211}$ and $R_{212}$ are each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ are each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ are each independently selected from a hydrogen atom, a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 is 1 or 2.

In Chemical Formulae 201A and 201A-1, $R_{213}$ and $R_{214}$ may be bonded to each other to form a saturated or unsaturated ring.

The compound represented by Chemical Formula 201 and the compound represented by Chemical Formula 202 may each independently include Compounds HT1 to HT20 below, without being limited thereto.

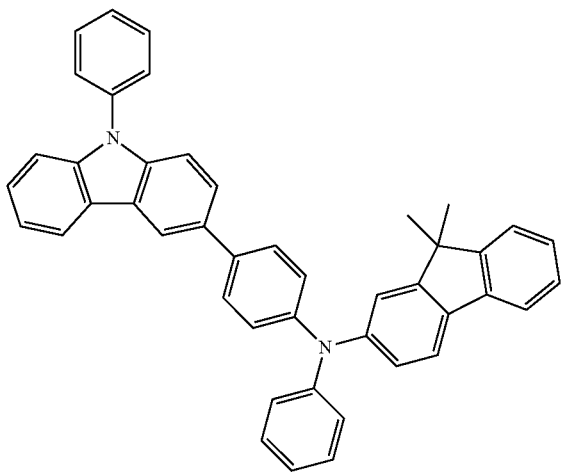

HT1

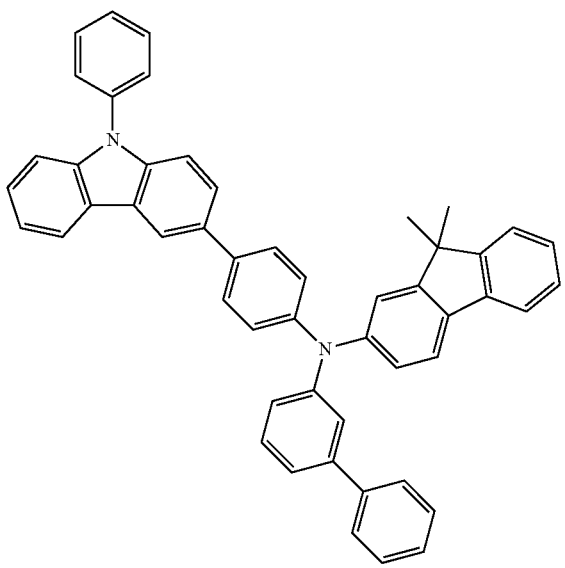

HT2

HT3
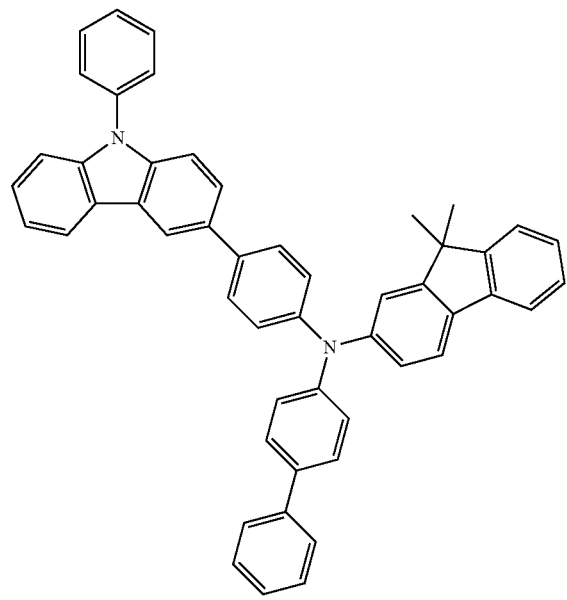
HT5
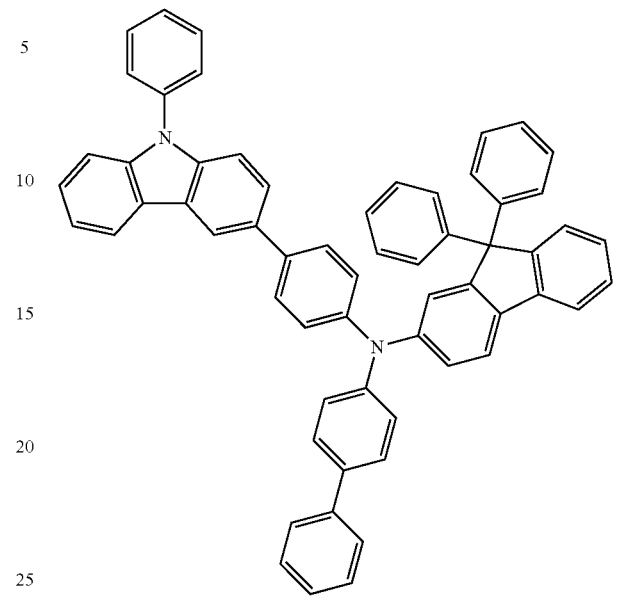
HT4
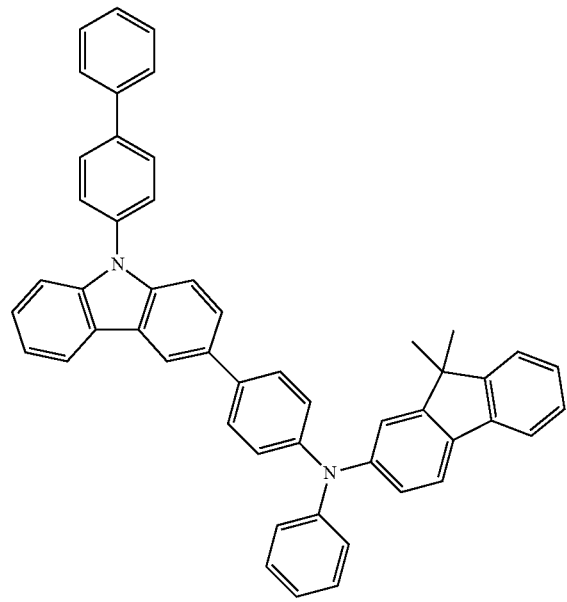
HT6
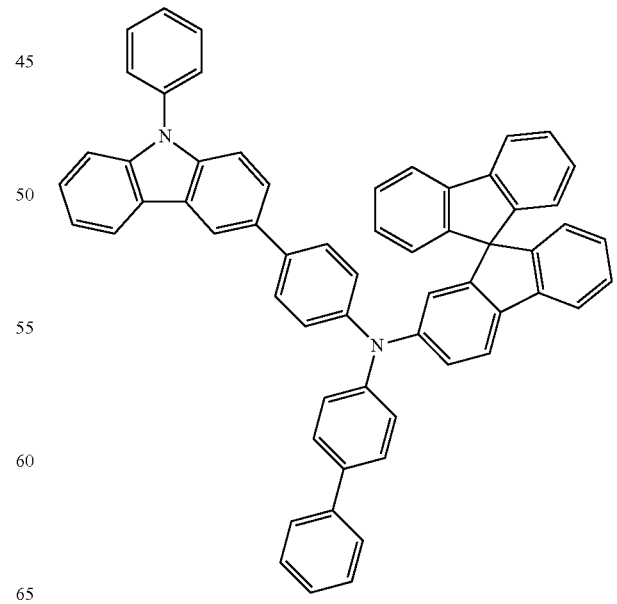

HT7
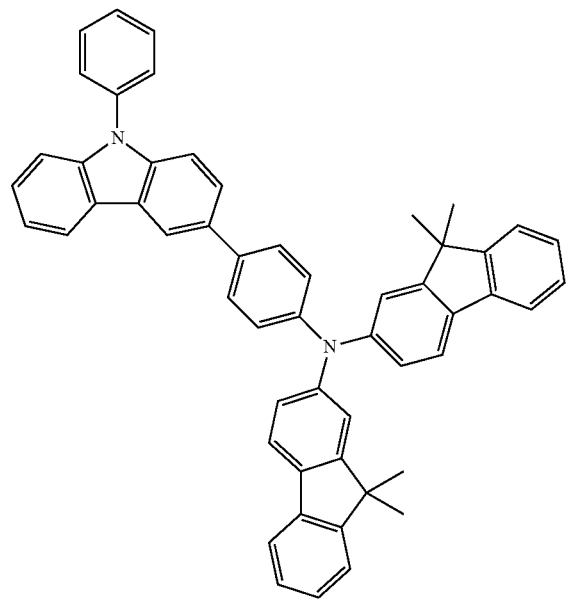
HT9
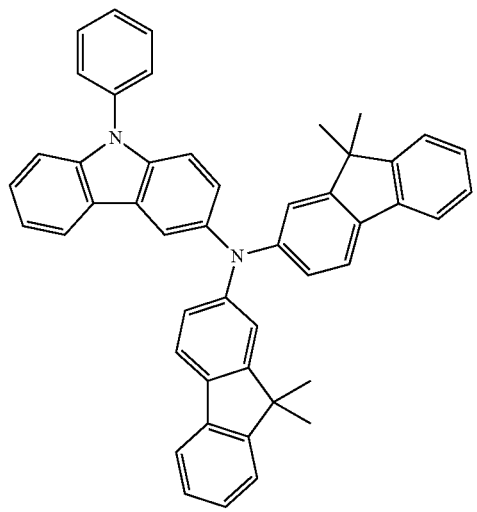
HT8
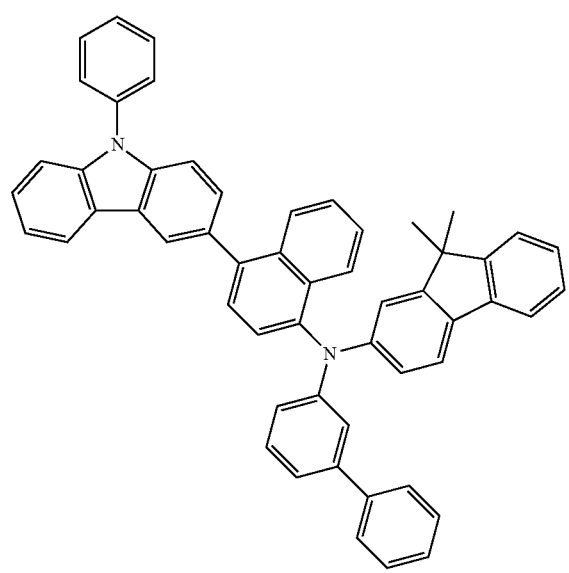
HT10
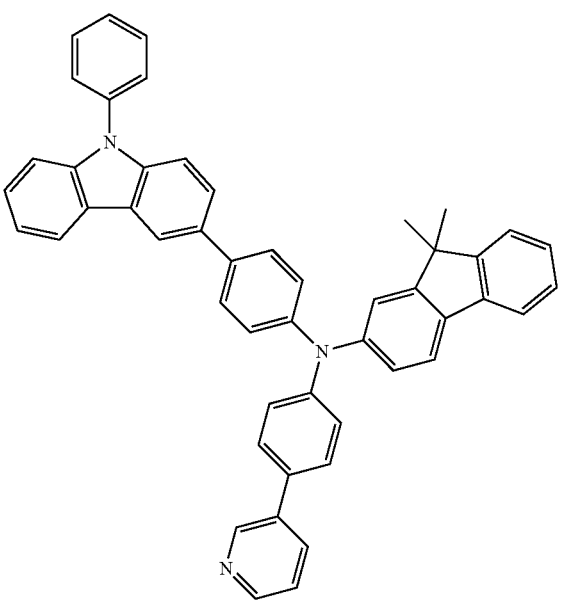

HT11
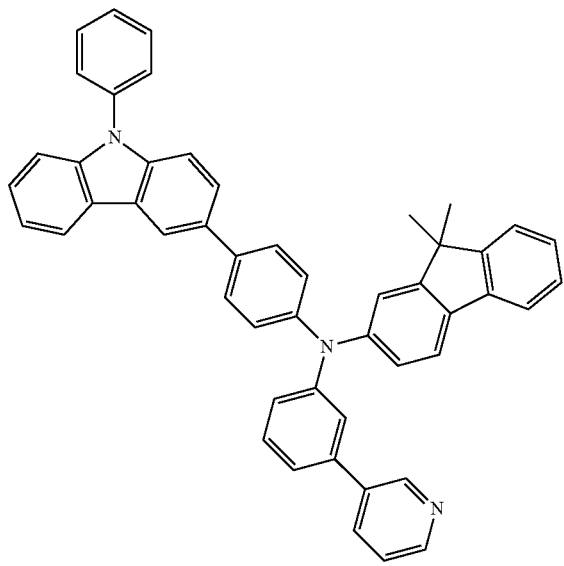
HT14
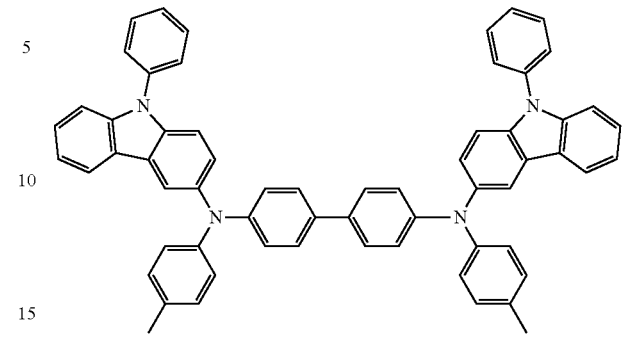
HT15
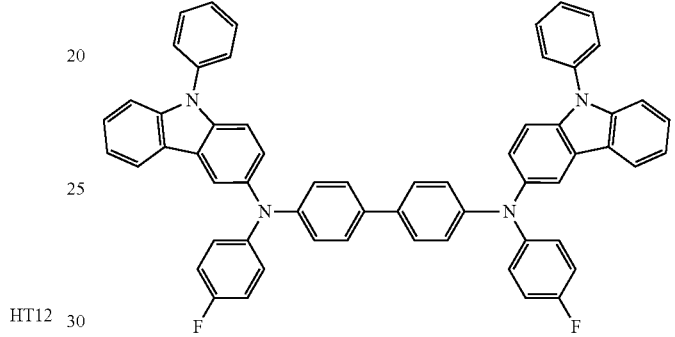
HT12
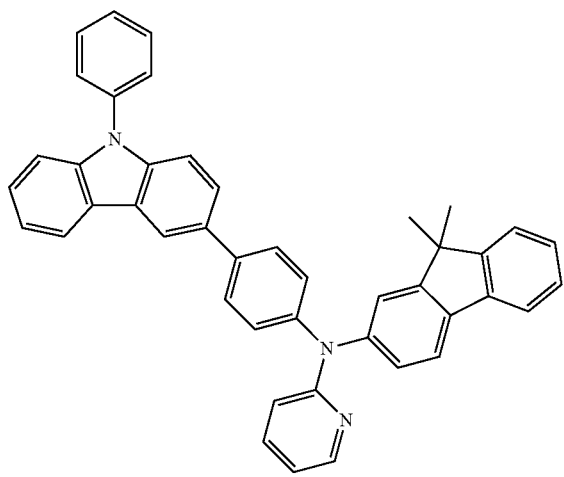
HT16
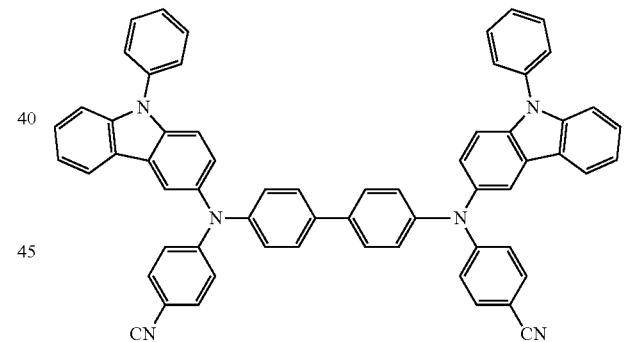
HT13
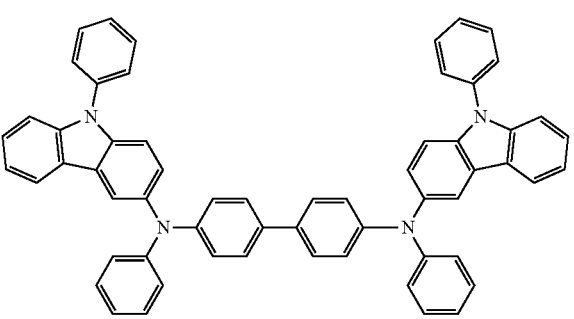
HT17
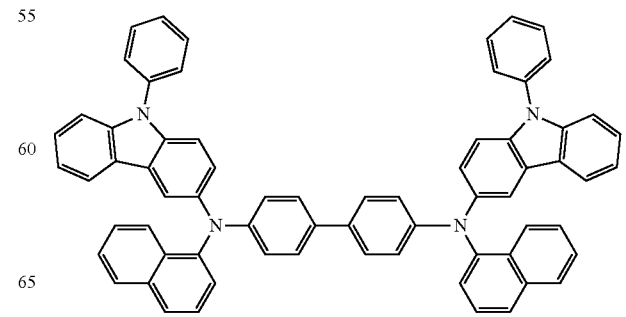

-continued

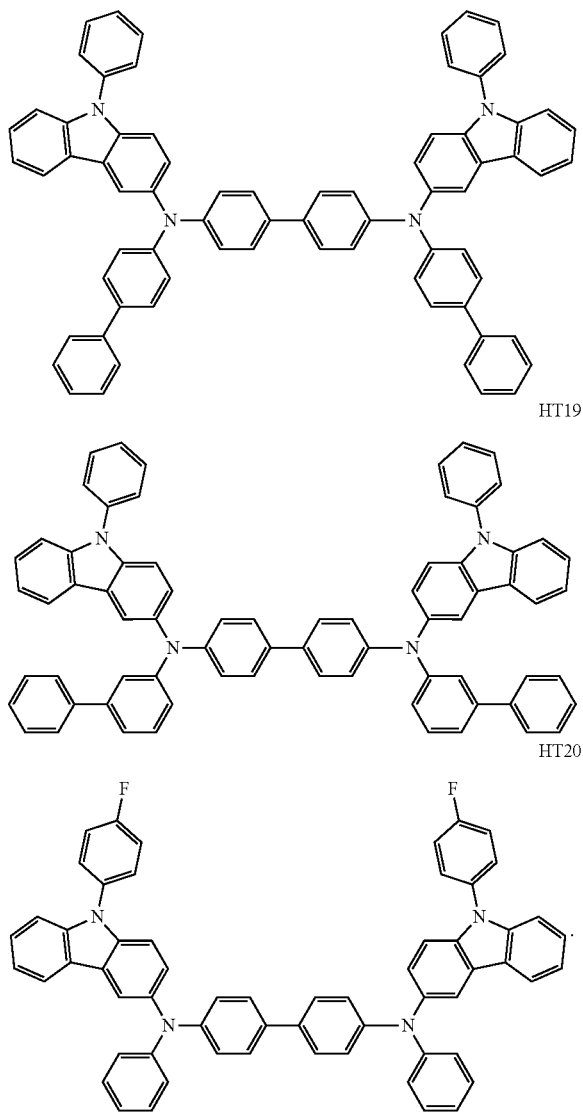

HT18

HT19

HT20

The hole transport region may have a thickness of about 100 Å to about 10,000 Å, for example, about 100 Å to about 1,000 Å. When the hole transport region includes both of the HIL and the HTL, the HIL may have a thickness of about 100 Å to about 10,000 Å, for example, about 100 Å to about 9,950 Å, or about 100 Å to about 1,000 Å, and the HTL may have a thickness of about 50 Å to about 2,000 Å, for example, about 100 Å to about 1,500 Å. When the thicknesses of the hole transport region, the HIL, and the HTL are within any of the ranges described above, hole transporting ability may be improved without a substantial increase in driving voltage.

The hole transport region may further include a charge-generating material to improve conductivity, in addition to the materials described above. The charge-generating material may be dispersed in the hole transport region uniformly or non-uniformly.

For example, the charge-generating material may be a p-dopant. The p-dopant may be a quinone derivative, a metal oxide, or a cyano group-containing compound, without being limited thereto. Non-limiting examples of the p-dopant include quinone derivatives such as tetracyanoquinonedimethane (TCNQ) and/or 2,3,5,6-tetrafluoro-tetracyano-1,4-benzoquinonedimethane (F4-TCNQ); metal oxides such as tungsten oxide and/or molybdenum oxide; and Compound HT-D1 below:

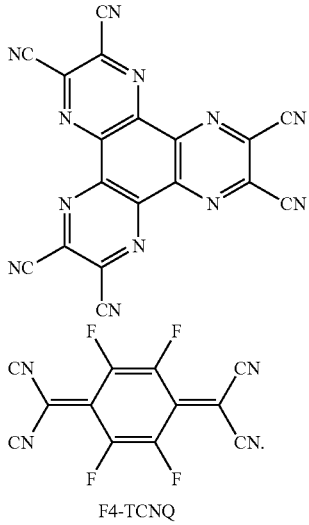

Compound HT-D1

F4-TCNQ

The hole transport region may further include at least one of a buffer layer and an EBL, in addition to the HIL and the HTL as described above. The buffer layer may increase light emitting efficiency by compensating an optical resonance distance according to a wavelength of light emitted from the EML. Any of the materials included in the hole transport region may be used in the buffer layer. The EBL may serve to block electron injection from the electron transport region.

The EML may be formed on the first electrode 110 or on the hole transport region by using one or more suitable methods such as vacuum deposition, spin coating, casting, LB technique, inkjet printing, laser printing, and/or LITI. When the EML is formed by vacuum deposition and/or spin coating, the deposition conditions and coating conditions may be similar to those for the formation of the HIL.

When the organic light-emitting device 10 is a full-color organic light-emitting device, the EML may be patterned into a red EML, a green EML, and a blue EML based on a sub-pixel. Alternatively, the EML may have a multi-layered structure in which a red EML, a green EML, and a blue EML are stacked upon one another, or a single-layered structure in which a red light-emitting material, a green light-emitting material, and a blue light-emitting material are mixed so as to emit white light.

The EML may include a host and a dopant. At least one of the host and the dopant may be the compound for an organic light-emitting device that satisfies Mathematical Formula 1.

In some embodiments, the EML may include a first host, a second host, and a dopant. At least one of the first host and the dopant may be the compound for an organic light-emitting device that satisfies Mathematical Formula 1.

A weight ratio of the host to the dopant in the EML may be from about 50:50 to about 99:1, for example, about 85:15 to about 98:2, without being limited thereto.

The EML may have a thickness of about 100 Å to about 1,000 Å, for example, about 200 Å to about 600 Å. When the thickness of the EML is within any of the ranges described above, light emitting ability may be improved without a substantial increase in driving voltage.

Then, the electron transport region may be positioned on the EML.

The electron transport region may include at least one selected from an HBL, an ETL, and an EIL, without being limited thereto.

For example, the electron transport region may have a structure of ETL/EIL or a structure of HBL/ETL/EIL, where the layers in each structure are sequentially stacked on the EML, but the electron transport region is not limited thereto.

According to some embodiments, the organic layer 150 of the organic light-emitting device includes the electron transport region between the EML and the second electrode 190, and the electron transport region may include at least one compound represented by Chemical Formula 1 (e.g., at least one condensed cyclic compound represented by Chemical Formula 1).

In some embodiments, the electron transport region may include the HBL. When a phosphorescent dopant is used in the EML, the HBL may help prevent or reduce the diffusion of triplet excitons or holes into the ETL.

When the electron transport region includes the HBL, the HBL may be formed on the EML by using one or more suitable methods such as vacuum deposition, spin coating, casting, LB technique, inkjet printing, laser printing, and/or LITI. When the HBL is formed by vacuum deposition and/or spin coating, the deposition conditions and coating conditions may be similar to those for the formation of the HIL.

For example, the HBL may include at least one of BCP and Bphen below, without being limited thereto.

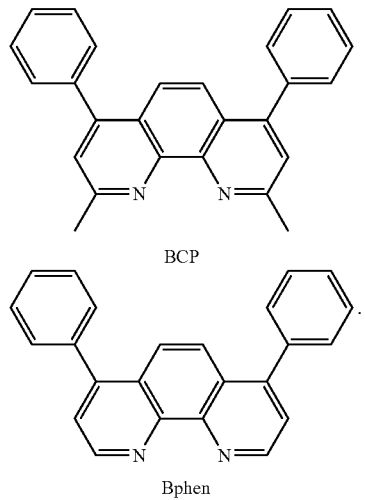

BCP

Bphen

The HBL may have a thickness of about 20 Å to about 1,000 Å, for example, about 30 Å to about 300 Å. When the thickness of the HBL is within any of the ranges described above, the HBL may have improved hole blocking ability without a substantial increase in driving voltage.

The electron transport region may further include the ETL. The ETL may be formed on the EML or on the HBL by using one or more suitable methods such as vacuum deposition, spin coating, casting, LB technique, inkjet printing, laser printing, and/or LITI. When the ETL is formed by vacuum deposition and/or spin coating, the deposition conditions and coating conditions may be similar to those for the formation of the HIL.

In some embodiments, the ETL may include at least one selected from a compound represented by Chemical Formula 601 and a compound represented by Chemical Formula 602.

$$Ar_{601}\text{-}[(L_{601})_{xe1}\text{-}E_{601}]_{xe2}.$$ Chemical Formula 601

In Chemical Formula 601, $Ar_{601}$ is selected from naphthalene, heptalene, fluorene, spiro-fluorene, benzofluorene, dibenzofluorene, phenalene, phenanthrene, anthracene, fluoranthene, triphenylene, pyrene, chrysene, naphthacene, picene, perylene, pentaphene, and indenoanthracene; and naphthalene, heptalene, fluorene, spiro-fluorene, benzofluorene, dibenzofluorene, phenalene, phenanthrene, anthracene, fluoranthene, triphenylene, pyrene, chrysene, naphthacene, picene, perylene, pentaphene, and indenoanthracene, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, and —Si($Q_{301}$)($Q_{302}$)($Q_{303}$), where $Q_{301}$ to $Q_{303}$ are each independently a hydrogen atom, a $C_1$-$C_{60}$ alkyl group, a $C_2$-$C_{60}$ alkenyl group, a $C_6$-$C_{60}$ aryl group, or a $C_2$-$C_{60}$ heteroaryl group;

$L_{601}$ is as described above with reference to $L_{201}$;

$E_{601}$ is selected from a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, an heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronelyl group, an ovalenyl group, a pyrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

xe1 is selected from 0, 1, 2, and 3;
xe2 is selected from 1, 2, 3, and 4.

Chemical Formula 602

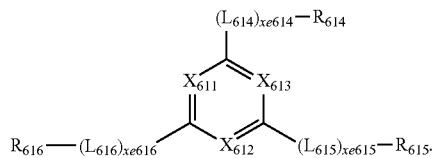

In Chemical Formula 602, $X_{611}$ is N or C-$(L_{611})_{xe611}$-$R_{611}$, $X_{612}$ is N or C-$(L_{612})_{xe612}$-$R_{612}$, $X_{613}$ is N or C-$(L_{613})_{xe613}$-$R_{613}$, and at least one of $X_{611}$ to $X_{613}$ is N;

$L_{611}$ to $L_{616}$ are as described above with reference to $L_{201}$;

$R_{611}$ to $R_{616}$ are each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, —F, —Cl, —Br, —I, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 are each independently selected from 0, 1, 2 and 3.

The compound represented by Chemical Formula 601 and the compound represented by Chemical Formula 602 may be each independently selected from Compounds ET1 to ET15 below, but are not limited thereto.

ET1

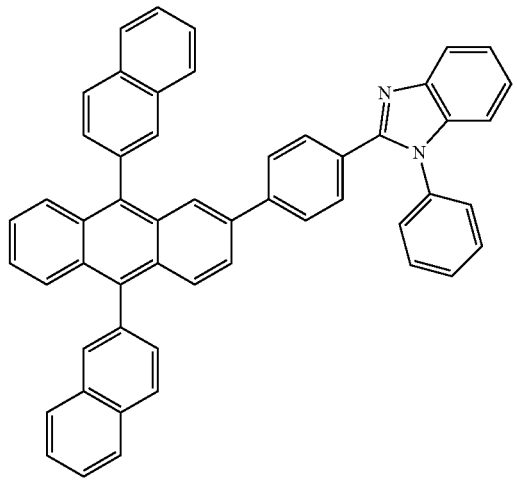

ET2
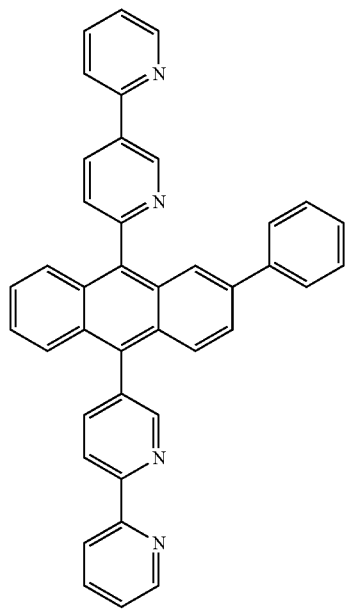
ET3
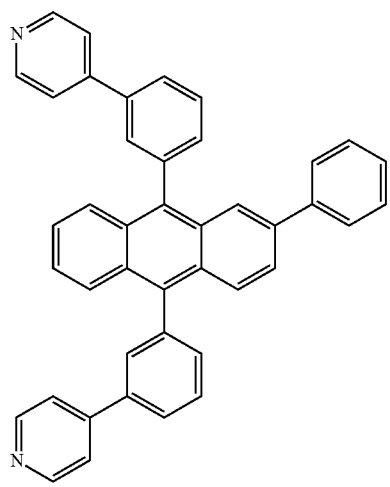
ET4
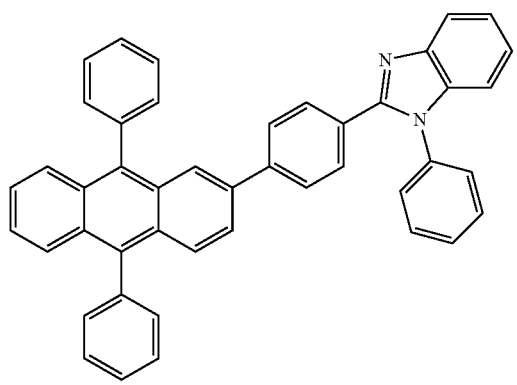
ET5
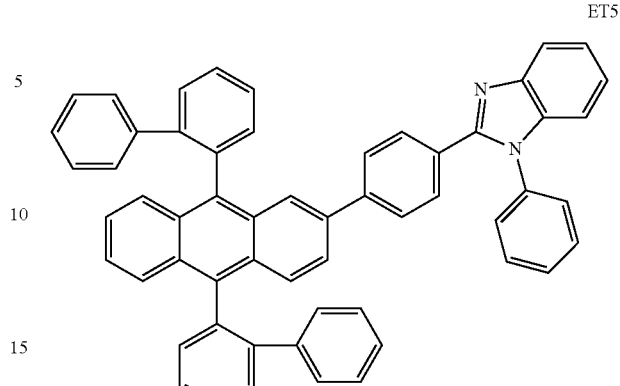
ET6
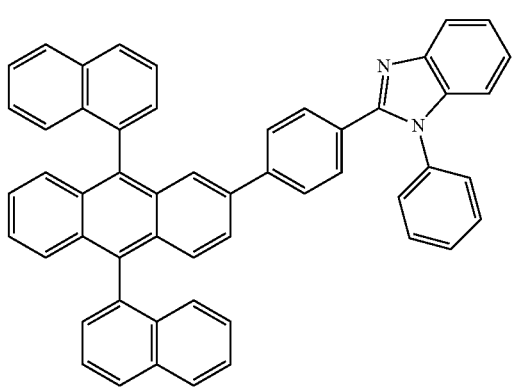
ET7
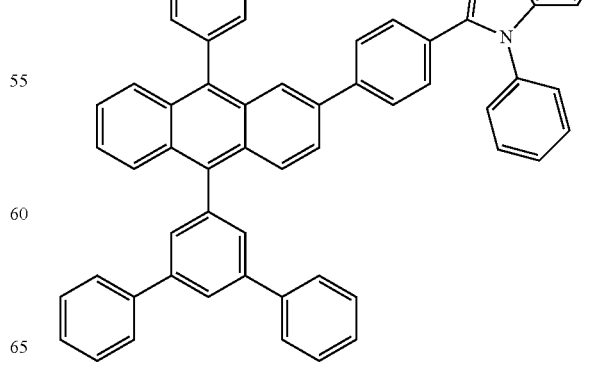

ET8
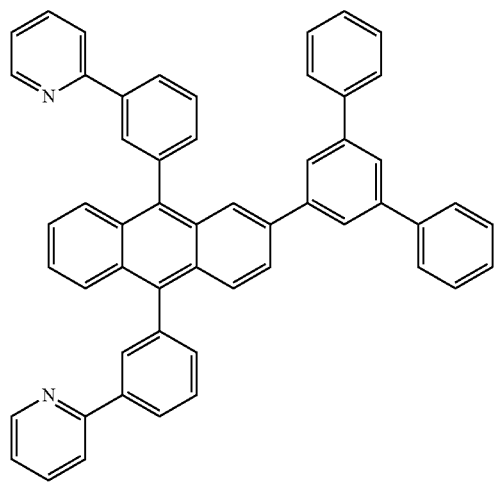
ET9
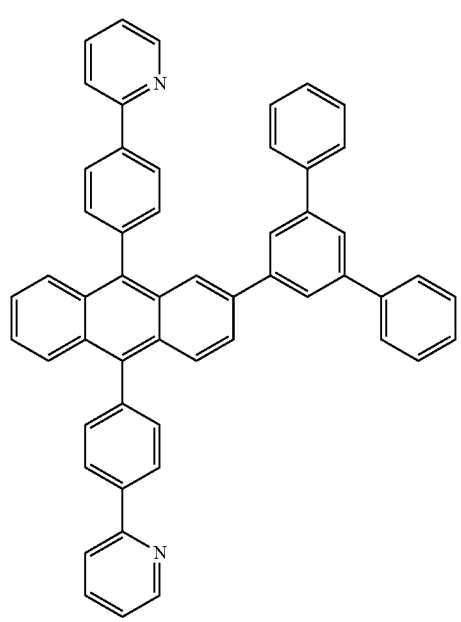
ET10
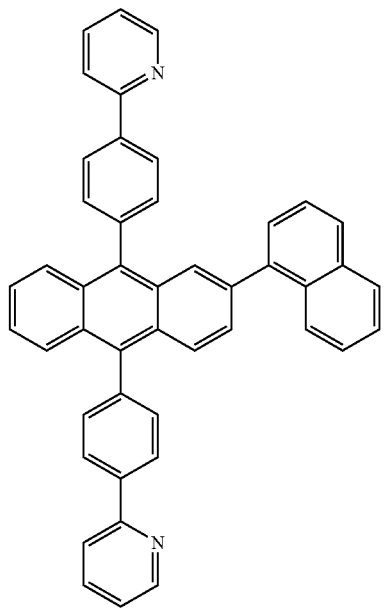
ET11
ET12
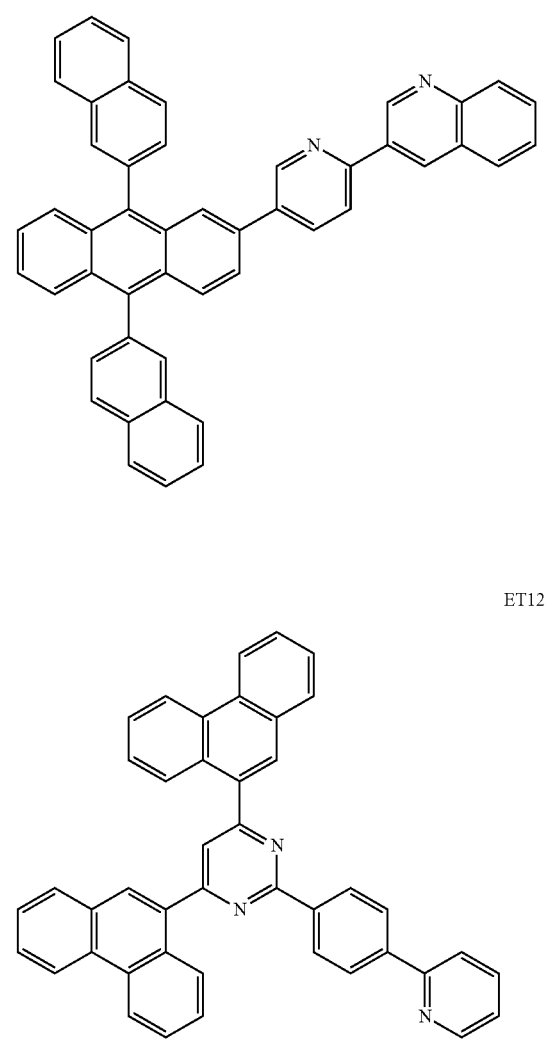

ET13

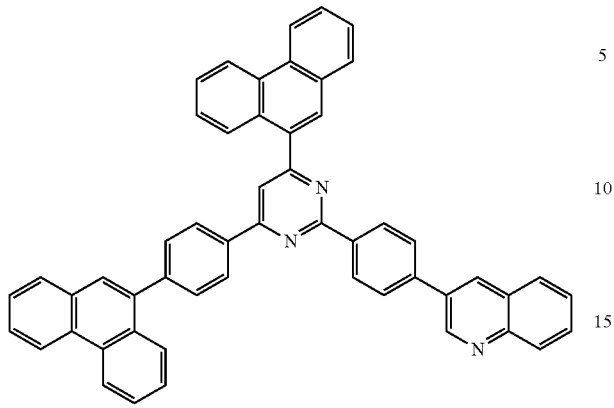

ET14

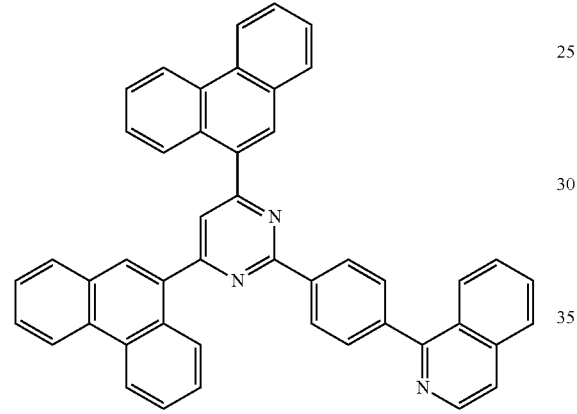

ET15

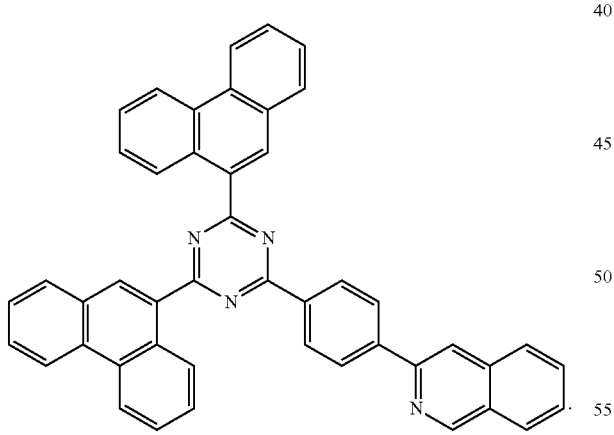

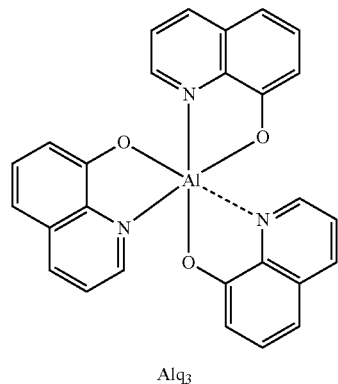

Alq₃

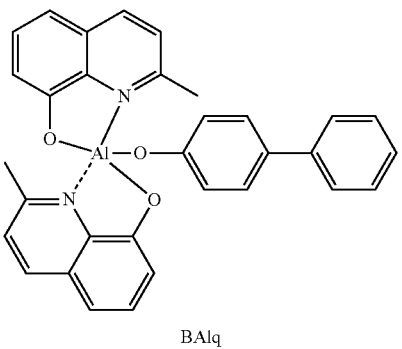

BAlq

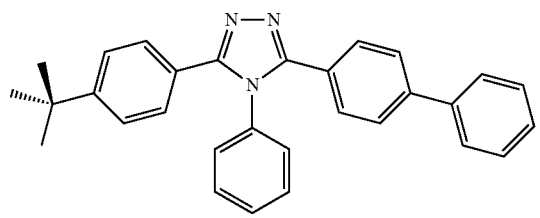

TAZ

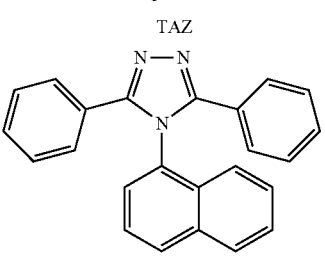

NTAZ

According to some embodiments, the organic layer 150 of the organic light-emitting device includes the electron transport region between the EML and the second electrode 190, the electron transport region includes the ETL, and the ETL includes at least one compound represented by Chemical Formula 1 (e.g., at least one condensed cyclic compound represented by Chemical Formula 1).

Alternatively, the ETL may include at least one selected from BCP, Bphen, Alq₃, Balq, TAZ, and NTAZ.

The ETL may have a thickness of about 100 Å to about 1,000 Å, for example, about 150 Å to about 500 Å. When the thickness of the ETL is within any of the ranges described above, electron transporting ability may be improved without a substantial increase in driving voltage.

The ETL may further include a metal-containing material, in addition to the materials described above.

The metal-containing material may include a Li complex. The Li complex may include Compound ET-D1 (lithium quinolate (LiQ)) or Compound ET-D2 below.

ET-D1

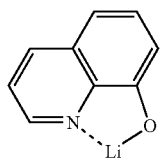

ET-D2

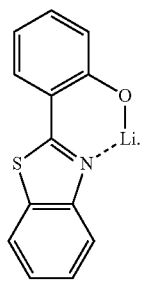

The electron transport region may further include an EIL capable of facilitating electron injection from the second electrode 190.

The EIL may be formed on the ETL by using one or more suitable methods such as vacuum deposition, spin coating, casting, LB technique, inkjet printing, laser printing, and/or LITI. When the EIL is formed by vacuum deposition and/or spin coating, the deposition conditions and coating conditions may be similar to those for the formation of the HIL.

The EIL may include at least one selected from LiF, NaCl, CsF, $Li_2O$, BaO, and LiQ.

The EIL may have a thickness of about 1 Å to about 100 Å, for example, about 3 Å to about 90 Å. When the thickness of the EIL is within any of the ranges described above, electron injection ability may be improved without a substantial increase in driving voltage.

In some embodiments, the second electrode 190 is positioned on the organic layer 150. The second electrode 190 may be a cathode, which is an electron injecting electrode. A material used to form the second electrode 190 may be a metal, an alloy, an electrically conductive compound, which all have a low work function, or a mixture thereof. Non-limiting examples of the material used to form the second electrode 190 may include lithium (Li), magnesium (Mg), aluminum (Al), aluminum (AD-lithium (Li), calcium (Ca), magnesium (Mg)-indium (In), and magnesium (Mg)-silver (Ag). Alternatively, ITO or IZO may be used to form the second electrode 190. The second electrode 190 may be a reflective, semi-transmissive, or transmissive electrode.

Although the organic light-emitting device has been described above with reference to FIG. 1, embodiments of the present disclosure are not limited thereto.

In some embodiments, internal quantum efficiency $QE_i$ of the organic light-emitting device may be greater than 40% and less than 62.5%, without being limited thereto.

In some embodiments, external quantum efficiency $QE_o$ of the organic light-emitting device may be greater than 8% and equal to or less than 32%.

The external quantum efficiency $QE_o$ may be calculated using the following Mathematical Formula 4, without being limited thereto.

External quantum efficiency ($QE_o$)=Internal quantum efficiency ($QE_i$)×Out-coupling efficiency  Mathematical Formula 4

In Mathematical Formula 4, out-coupling efficiency is in a range of about 20% to about 50%.

As used herein, the $C_1$-$C_{10}$ alkyl group refers to a monovalent linear or branched aliphatic hydrocarbon group having 1 to 10 carbon atoms in the main chain, and non-limiting examples thereof include a methyl group, an ethyl group, a propyl group, an isobutyl group, a sec-butyl group, a tert-butyl group, a pentyl group, an iso-amyl group, and a hexyl group.

As used herein, the $C_6$-$C_{15}$ aryl group refers to a monovalent carbocyclic aromatic system having 6 to 15 carbon atoms as ring-forming atoms. Non-limiting examples of the $C_6$-$C_{10}$ aryl group include a phenyl group, a naphthyl group, an anthracenyl group, and a phenanthrenyl group.

As used herein, the $C_1$-$C_{15}$ heteroaryl group refers to a monovalent group having a carbocyclic aromatic system including at least one hetero atom selected from N, O, P, and S and 1 to 15 carbon atoms as ring-forming atoms. Non-limiting examples of the $C_1$-$C_{15}$ heteroaryl group may include a pyridinyl group, a pyrimidinyl group, a pyrazinyl group, a pyridazinyl group, a triazinyl group, a quinolinyl group, and an isoquinolinyl group. When the $C_1$-$C_{15}$ heteroaryl group includes two or more rings, the rings may be fused to each other.

EXAMPLES

Synthesis Example 1

Synthesis of Compound 5

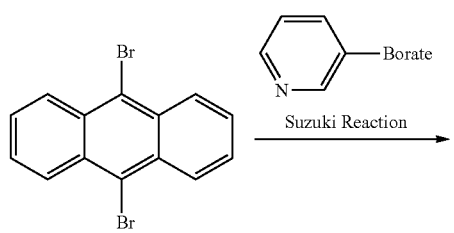

-continued

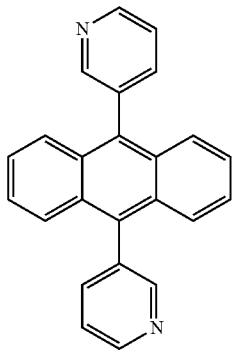

10 g of 9,10-dibromoanthracene (0.0298 mol), 13.42 g of 3-(4,4,5,5-tetramethyl-1,3,2-dioxaborane-2-yl)pyridine (0.0665 mol), and 2 M $K_2CO_3$ were dissolved in 10 mL of toluene, and a small amount of $Pd(pph_3)_4$ was added thereto. The mixture was maintained at 90° C. for 24 hours. Then, reactions were terminated by adding water to the solution. The resulting reaction mixture was extracted using ether, and the ether was then removed from the resulting organic phase, thereby obtaining a crude product. The crude product was purified by silica-gel column chromatography using an eluate including hexane and ethyl acetate (EA) in a volume ratio of 1:10, and recrystallized using ether to obtain Compound 5 (yield: 56%). The obtained Compound 5 was identified by NMR.

H-NMR ($CDCl_3$, 300 Mhz) 9.24 (2H), 8.70 (2H), 7.57 (2H), 8.42 (2H), 8.20 (4H), 7.47 (4H).

Evaluation Example 1

Evaluation of Energy Level of First Singlet Energy (S1), First Triplet Energy (T1), and Second Triplet Energy (T2)

S1, T1 and T2 energy levels of each of Compound 5 and ADN were evaluated according to the method as described in Table 3, and the results are shown in Table 4.

TABLE 3

| Evaluation method of S1 energy level | Each compound was mixed with toluene (1 mg of each compound was dissolved in 3 cc of toluene) and added to a quartz cell, and photoluminescence spectrum of each mixture (compound with toluene) was measured at room temperature by using a photoluminescence meter. Then, a value of S1 energy level was obtained by dividing 1240 by a peak maximum wavelength. |
|---|---|
| Evaluation method of T1 energy level | Each compound was mixed with toluene (1 mg of each compound was dissolved in 3 cc of toluene) and added to a quartz cell, and photoluminescence spectrum of each mixture (compound with toluene) was measured in liquid nitrogen (at 77 K) by using a photoluminescence meter. The measured value was compared with the one obtained at room temperature, and only the peak observed at a low temperature was analyzed, thereby calculating T1 energy level. |
| Evaluation method of T2 energy level | Since there is no method of accurately calculating T2 energy level, T2 energy level was replaced with a value calculated using B3LYP/6-31G base set by using Gaussian 09'. |

TABLE 4

| Compound | S1 energy level (eV) - measurement value | T1 energy level (eV) - measurement value | T2 energy level (eV) - calculated value |
|---|---|---|---|
| Compound No. 5 | 2.85 | 1.71 | 3.43 |
| ADN | 2.92 | 1.73 | 2.67 |

As results in Table 4 illustrate, Compound 5 has electrical properties suitable for a material used to form the organic light-emitting device. In addition, Compound 5 satisfies Mathematical Formula 1, while ADN cannot satisfy Mathematical Formula 1.

Example 1

An ITO glass substrate (Corning) having a thickness of 15 $\Omega/cm^2$ (1200 Å) and including an ITO layer was cut to a size of 50 mm×50 mm×0.7 mm, sonicated for five minutes in each of isopropyl alcohol and purified water, and then cleaned by exposure to UV rays for 30 minutes and exposure to ozone. The resulting ITO glass substrate was then installed in a vacuum deposition apparatus.

Then, m-MTDATA was deposited on the ITO anode (substrate) to form an HIL having a thickness of 600 Å, and then NPB was deposited on the HIL to form an HTL having a thickness of 300 Å, and Compound 5 as a host and BCzVBi as a dopant were co-deposited on the HTL in a weight ratio of 90:10 to form an EML having a thickness of 300 Å.

Then, $Alq_3$ was deposited on the EML to form an ETL having a thickness of 300 Å, and LiF was deposited on the ETL to form an EIL having a thickness of 10 Å. Then, Al was deposited on the EIL to form a second electrode (cathode) having a thickness of 1,000 Å. As a result, an organic light-emitting device was prepared.

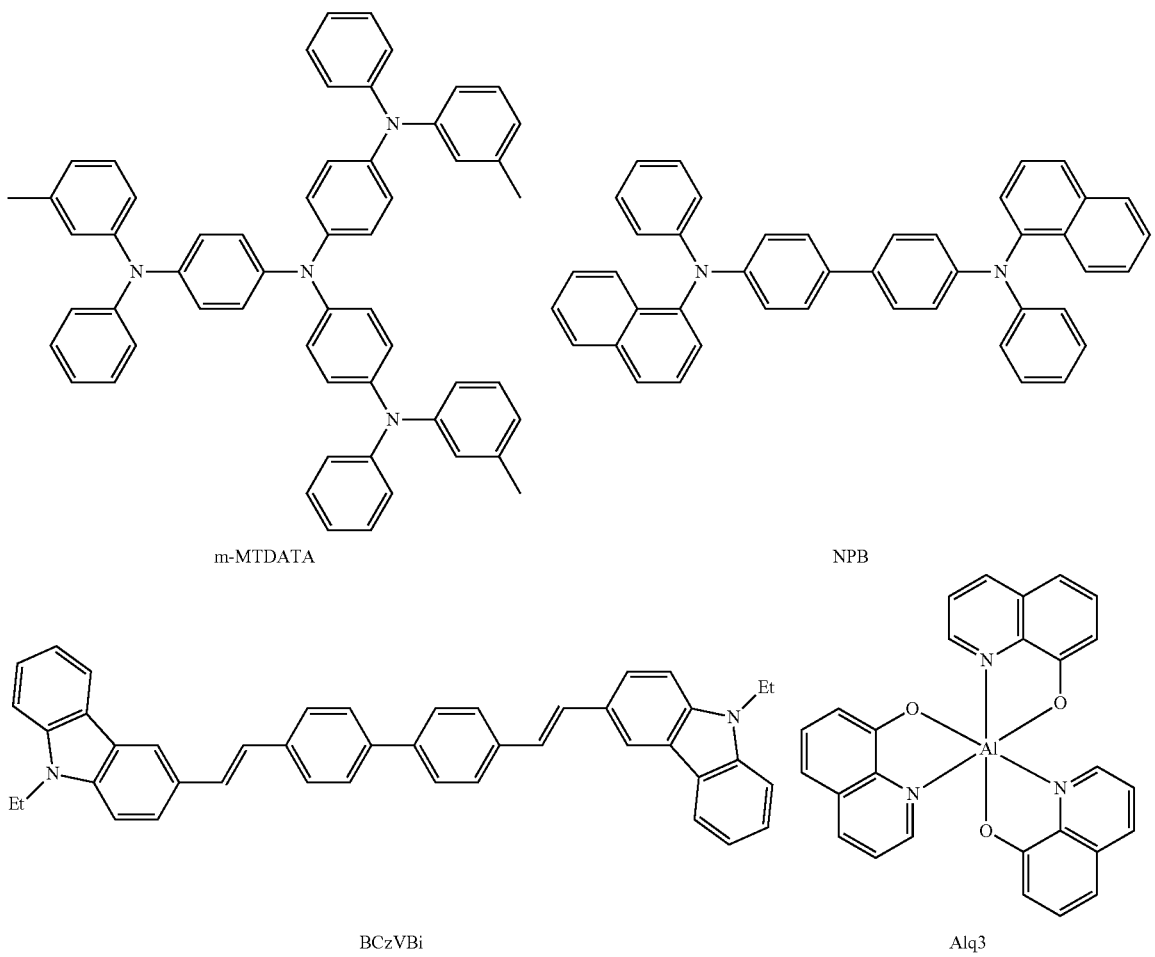

m-MTDATA

NPB

BCzVBi

Alq3

Comparative Example 1

An organic light-emitting device was prepared in the same (or substantially the same) manner as in Example 1, except that ADN was used instead of Compound 5 in the formation of the EML.

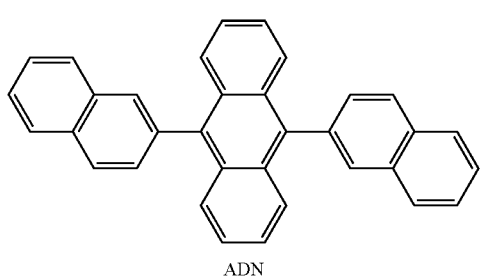 [SMILES: c1ccc2cc(-c3c4ccccc4c(-c4ccc5ccccc5c4)c4ccccc34)ccc2c1]

ADN

Evaluation Example 2

Evaluation of External Quantum Efficiency

External quantum efficiency of each of the organic light-emitting devices prepared according to Example 1 and Comparative Example 1 was measured using a QS1000-IVLQ measurer, and the results are shown in Table 5.

TABLE 5

| | External quantum efficiency (%) |
|---|---|
| Example 1 | 9.1% |
| Comparative Example 1 | 4.8% |
| Theoretical maximum value* | 8% |

Theoretical maximum value* of external quantum efficiency was obtained when the conditions according to an exemplary embodiment were not satisfied and calculated using Mathematical Formula 5 below.

Theoretical maximum value*=Charge balance (100%)×exciton creating efficiency (40%)×light emitting quantum efficiency (100%)×light emitting efficiency (20%)=8%   Mathematical Formula 5

As illustrated in Table 5, the external quantum efficiency of the organic light-emitting device according to Example 1 was significantly better than that of the organic light-emitting device according to Comparative Example 1. In addition, the external quantum efficiency of the organic light-emitting device according to Example 1 was better than the theoretical maximum value.

Evaluation Example 3

Evaluation of Delayed Fluorescence Rate

Figure 3:
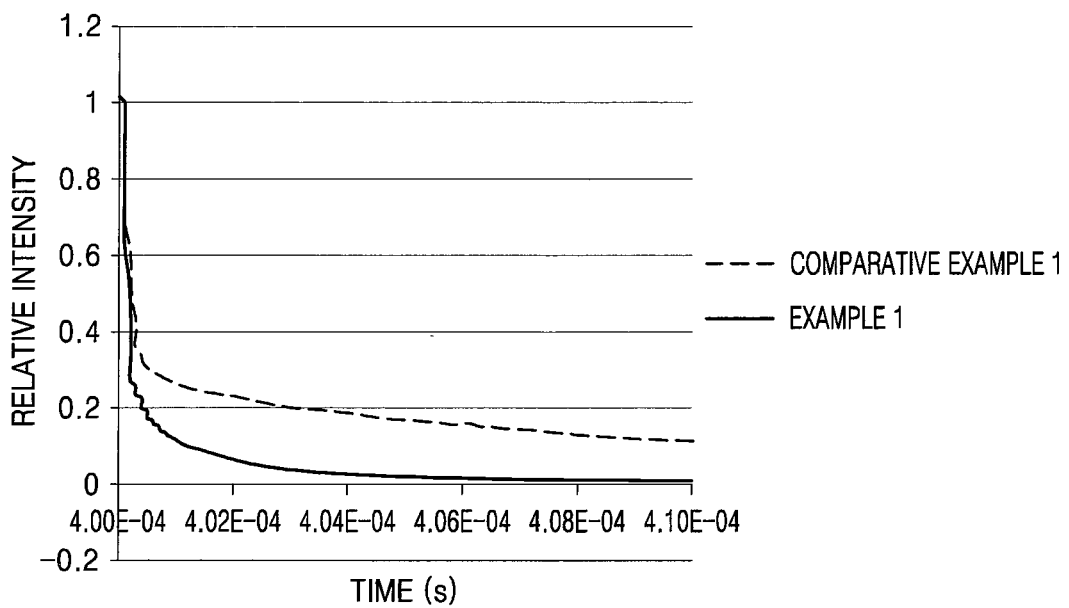
FIG. 3 is a graph illustrating transient electroluminescence (EL) analysis results of organic light-emitting devices according to Example 1 and Comparative Example 1.
Figure 4:
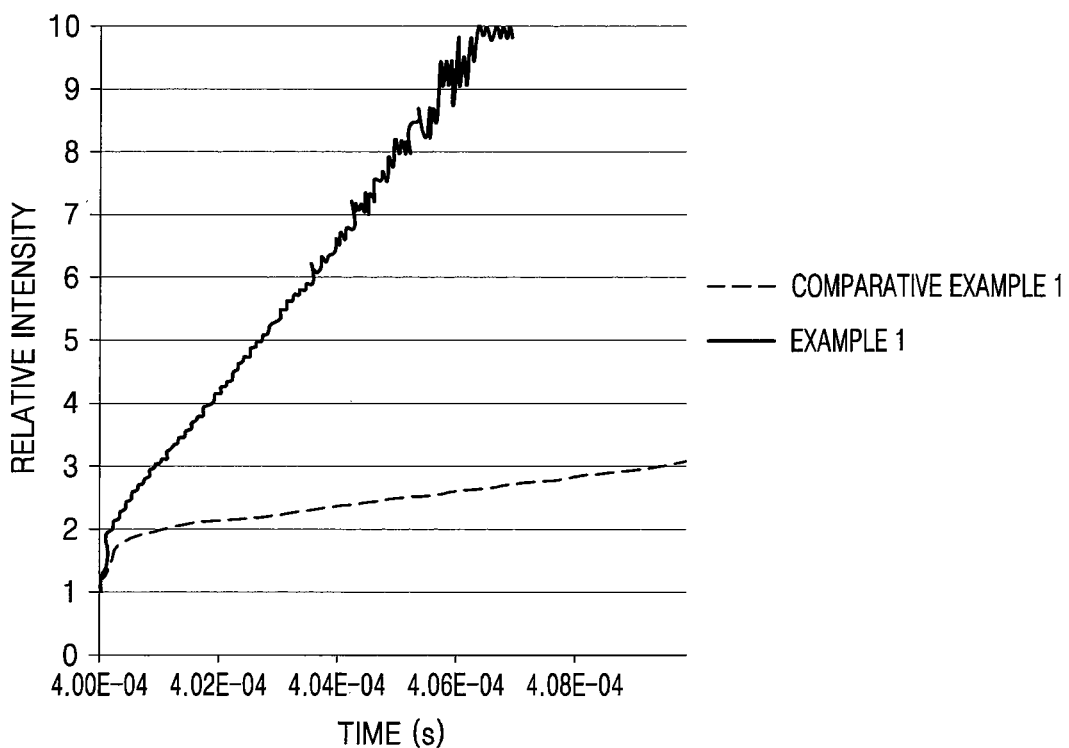
FIG. 4 is a graph illustrating the graph values of FIG. 3 converted using a 1/(square root) function.

Transient electroluminescence (EL) was measured with respect to each of the organic light-emitting devices of Example 1 and Comparative Example 1. Voltage used for the measurement was driving voltage at a required brightness, and light intensity was measured after applying a pulse of 400 μs at a frequency of 10 Hz. The results are shown in FIG. 3. The values of the graph of FIG. 3 were converted using a 1/(square root) function and the results are shown in FIG. 4. Delayed fluorescence rate was obtained using 1/(intercept)$^2$ calculated from FIG. 4, and the results are shown in Table 6.

TABLE 6

|  | Delayed fluorescence rate (%) |
| --- | --- |
| Example 1 | 25% |
| Comparative Example 1 | 52.5 |
| Theoretical maximum value** | 40% |

Theoretical maximum value** of excitons creating efficiency of 40% was obtained when conditions according to an exemplary embodiment were not satisfied.

As results in Table 6 illustrate, delayed fluorescence of the organic light-emitting device according to Example 1 was significantly better than that of the organic light-emitting device according to Comparative Example 1. In addition, the delayed fluorescence of the organic light-emitting device according to Example 1 was better than the theoretically maximum value.

As described above, according to one or more embodiments of the present disclosure, the organic light-emitting device including the compound for an organic light-emitting device may have high efficiency characteristics.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims, and equivalents thereof.

What is claimed is:

1. A compound for an organic light-emitting device, the compound satisfying Mathematical Formula 1 and being represented by one selected from the group consisting of Chemical Formulae 1A-1 to 1A-6:

Chemical Formula 1A-1

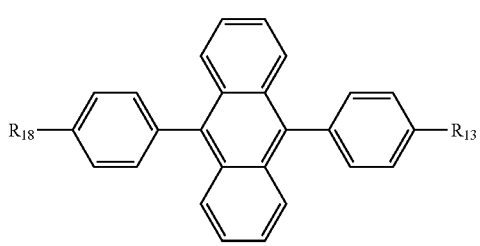

Chemical Formula 1A-2

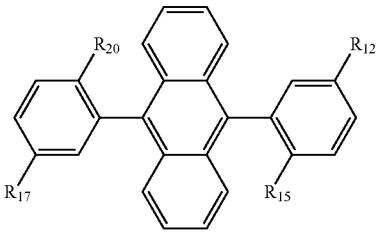

Chemical Formula 1A-3

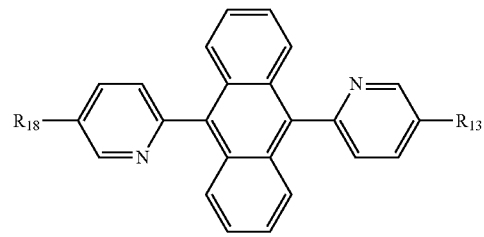

Chemical Formula 1A-4

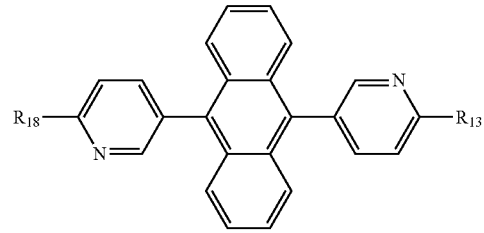

Chemical Formula 1A-5

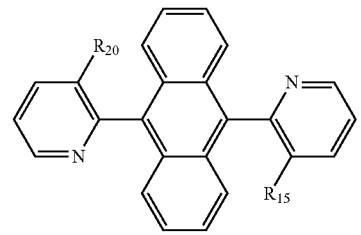

Chemical Formula 1A-6

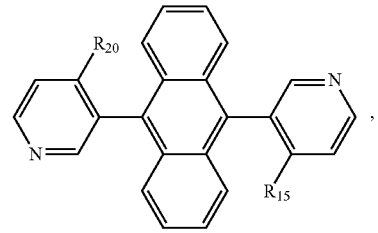

wherein, in Chemical Formulae 1A-1 and 1A-2, $R_{12}$, $R_{13}$, $R_{15}$, $R_{17}$, $R_{18}$ and $R_{20}$ are each independently selected from the group consisting of —F, a methyl group, an ethyl group, an n-propyl group, an iso-propyl group, an n-butyl group, an iso-butyl group, a sec-butyl group, a tert-butyl group, —Si(CH$_3$)$_3$, and compounds represented by Chemical Formulae 3-1 and 3-2, and in Chemical Formulae 1A-3 to 1A-6, $R_{12}$, $R_{13}$, $R_{15}$, $R_{17}$, $R_{18}$ and $R_{20}$ are each independently selected from the group consisting of a hydrogen atom, —F, a methyl group, an ethyl group, an n-propyl group, an iso-propyl group, an n-butyl group, an iso-butyl group, a sec-butyl group, a tert-butyl group, —Si(CH$_3$)$_3$, and compounds represented by Chemical Formulae 3-1 and 3-2:

3-1
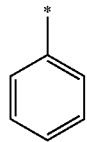

3-2
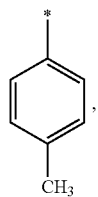

wherein, in Chemical Formulae 3-1 and 3-2,

* is a binding site to an adjacent atom;

$$E_{S1} < 2E_{T1} < E_{T2},\quad \text{Mathematical Formula 1}$$

wherein, in Mathematical Formula 1, $E_{S1}$ is a first singlet energy of the compound, $E_{S1}$ being in a range of about 3.1 eV to about 3.3 eV;

$E_{T1}$ is a first triplet energy of the compound; and $E_{T2}$ is a second triplet energy of the compound.

2. The compound of claim 1, wherein Chemical Formulae 1A-1 to 1A-6 satisfy Chemical Formula 1, wherein a first triplet energy ($E_{AT1}$) of A and a first triplet energy ($E_{BT1}$) of B satisfy Mathematical Formula 2:

$$A\!\!-\!\!(B)_n,\quad \text{Chemical Formula 1}$$

$$E_{AT1} < E_{BT1}.\quad \text{Mathematical Formula 2}$$

3. The compound of claim 2, wherein a second triplet energy ($E_{AT2}$) of A and a first triplet energy ($E_{BT1}$) of B satisfy Mathematical Formula 3:

$$E_{AT2} < E_{BT1}.\quad \text{Mathematical Formula 3}$$

4. The compound of claim 1, wherein the compound is selected from Compounds 1 to 10:

1
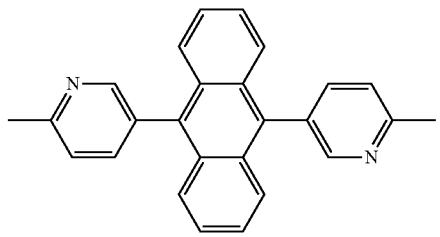

2
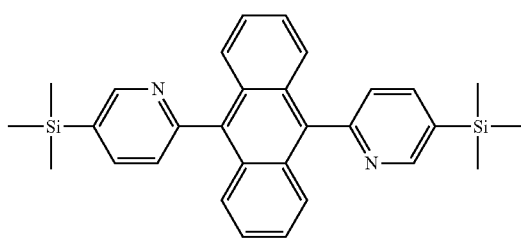

3
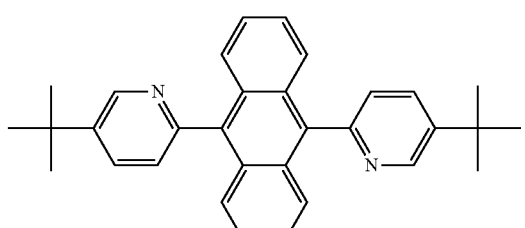

4
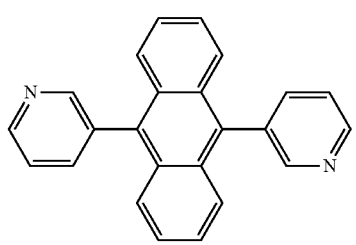

5
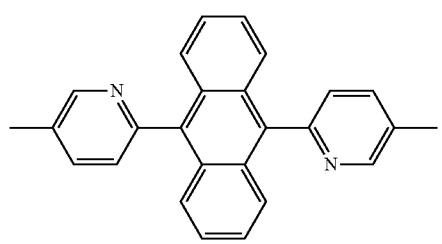

6
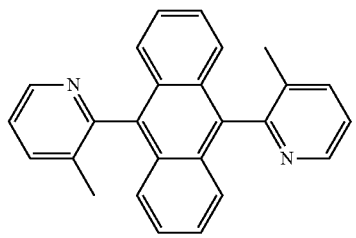

7
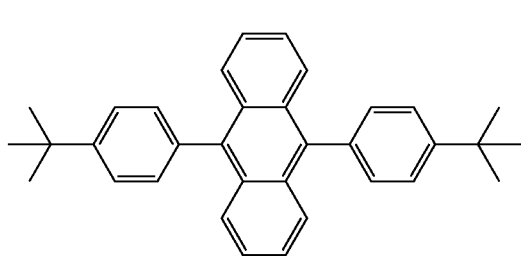

-continued

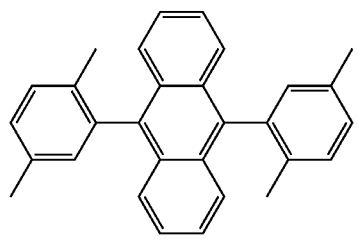

8

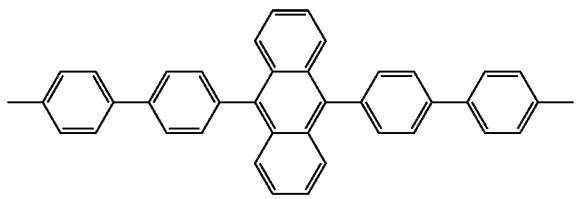

9

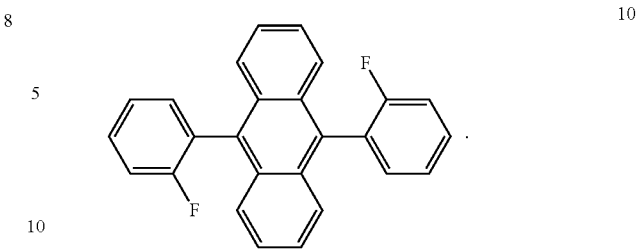

10

5. An organic light-emitting device comprising:
a first electrode;
a second electrode; and
an organic layer between the first electrode and the second electrode, the organic layer comprising an emission layer,
wherein the emission layer comprises the compound of claim 1.

6. The organic light-emitting device of claim 5, wherein the emission layer comprises a dopant and the compound as a host.

7. The organic light-emitting device of claim 5, wherein the emission layer comprises a host and the compound as a dopant.

8. The compound of claim 1, wherein
$E_{T1}$ is in a range of about 1.3 eV to about 1.7 eV, and
$E_{T2}$ is in a range of about 2.8 eV to about 3.5 eV.

* * * * *